(12) United States Patent
Schwartz et al.

(10) Patent No.: US 6,457,472 B1
(45) Date of Patent: *Oct. 1, 2002

(54) METHOD AND APPARATUS FOR PROVIDING VENTILATORY SUPPORT TO A PATIENT

(75) Inventors: Alan R. Schwartz; Philip L. Smith, both of Baltimore, MD (US)

(73) Assignee: The Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,106

(22) Filed: Dec. 11, 1997

Related U.S. Application Data

(60) Provisional application No. 60/033,322, filed on Dec. 12, 1996.

(51) Int. Cl.[7] .......................... A61M 16/00; A62B 7/00; F16K 31/02
(52) U.S. Cl. ............................ 128/204.23; 128/204.26; 128/207.14
(58) Field of Search ....................... 128/204.21, 204.23, 128/204.26, 207.14, 207.16

(56) References Cited

U.S. PATENT DOCUMENTS

| | | | |
|---|---|---|---|
| 2,584,450 A | 2/1952 | Holt et al. | |
| 3,682,166 A | 8/1972 | Jacobs | |
| 3,788,326 A | 1/1974 | Jacobs | |
| 3,794,026 A | 2/1974 | Jacobs | 128/204.18 |
| 3,991,762 A | 11/1976 | Radford | |
| 4,141,356 A | 2/1979 | Smargiassi | |
| 4,163,450 A | 8/1979 | Kirk et al. | |
| 4,224,939 A | 9/1980 | Lang | |
| 4,248,217 A | 2/1981 | Brisson | |
| 4,285,340 A * | 8/1981 | Gezari et al. | 128/205.24 |
| 4,305,388 A | 12/1981 | Brisson | |
| 4,456,008 A | 6/1984 | Clowson et al. | 128/205.19 |
| 4,459,982 A | 7/1984 | Fry | |
| 4,471,775 A * | 9/1984 | Clair et al. | 128/205.24 |
| 4,520,812 A | 6/1985 | Freitag et al. | |
| 4,552,142 A | 11/1985 | Hoffman et al. | |
| 4,565,194 A | 1/1986 | Weerda et al. | |
| 4,569,344 A | 2/1986 | Palmer | |
| 4,589,409 A | 5/1986 | Chatburn et al. | |
| 4,593,687 A | 6/1986 | Gray et al. | |
| 4,611,590 A | 9/1986 | Ryschka et al. | |
| 4,638,539 A | 1/1987 | Palmer | |

(List continued on next page.)

FOREIGN PATENT DOCUMENTS

EP     0 266 051     5/1988

OTHER PUBLICATIONS

McPherson et al., Respiratory Therapy Equipment, 2nd ed. CV Mosby Co. pp. 22–32, Feb. 1982.*

(List continued on next page.)

Primary Examiner—John G. Weiss
Assistant Examiner—Joseph F. Weiss, Jr.
(74) Attorney, Agent, or Firm—Alan G. Towner; Pietragallo, Bosick & Gordon

(57) ABSTRACT

A ventilatory support system which controls the flow of breathing gas to a patient based on the physiological requirements of the patient is disclosed. Gas pressure in the trachea of the patient is measured, and the delivery of breathing gas to the patient is controlled based on the sensed gas pressure. Depending on the physiological needs of the patient, a tracheal gas pressure limit and a breathing gas flow rate value are established. When the tracheal gas pressure limit is reached, the flow of breathing gas is reduced or terminated. The flow of breathing gas is resumed, for example, after a delay period, or after the tracheal gas pressure falls to a predetermined level.

56 Claims, 30 Drawing Sheets

U.S. PATENT DOCUMENTS

| | | | |
|---|---|---|---|
| 4,677,978 A | 7/1987 | Melker | |
| 4,682,010 A | 7/1987 | Drapeau et al. | |
| 4,682,591 A | 7/1987 | Jones | |
| 4,686,354 A | 8/1987 | Makin | |
| 4,686,974 A | 8/1987 | Sato et al. | |
| 4,696,296 A | 9/1987 | Palmer | 128/207.16 |
| 4,747,403 A | 5/1988 | Gluck et al. | 128/204.21 |
| 4,796,617 A | 1/1989 | Matthews et al. | |
| 4,805,611 A | 2/1989 | Hodgkins | |
| 4,825,859 A | 5/1989 | Lambert | |
| 4,838,259 A * | 6/1989 | Gluck et al. | 128/201.21 |
| 4,869,718 A | 9/1989 | Brader | |
| 4,898,163 A | 2/1990 | George | |
| 5,090,408 A | 2/1992 | Spofford et al. | |
| 5,101,820 A | 4/1992 | Christopher | |
| 5,134,995 A | 8/1992 | Gruenke et al. | |
| 5,148,802 A * | 9/1992 | Sanders et al. | 128/204.18 |
| 5,174,287 A | 12/1992 | Kallok et al. | |
| 5,181,509 A | 1/1993 | Spofford et al. | |
| 5,186,167 A * | 2/1993 | Kolobow | 128/207.14 |
| 5,186,168 A | 2/1993 | Spofford et al. | |
| 5,193,544 A * | 3/1993 | Jaffe | 128/634 |
| 5,199,424 A * | 4/1993 | Sullivan et al. | 128/204.18 |
| 5,199,427 A | 4/1993 | Strickland | |
| 5,218,957 A | 6/1993 | Strickland | |
| 5,245,995 A * | 9/1993 | Sullivan et al. | 128/204.23 |
| 5,255,675 A * | 10/1993 | Kolobow | 128/204.18 |
| 5,265,593 A * | 11/1993 | Odland | 128/204.18 |
| 5,297,288 A | 3/1994 | Christopher | |
| 5,333,606 A * | 8/1994 | Schneider et al. | 128/200.24 |
| 5,335,654 A | 8/1994 | Rapoport | |
| 5,367,292 A | 11/1994 | Szoke et al. | |
| 5,400,778 A * | 3/1995 | Jonson et al. | 128/205.19 |
| 5,419,314 A * | 5/1995 | Christopher | 128/200.26 |
| 5,433,193 A | 7/1995 | Sanders et al. | |
| 5,458,137 A | 10/1995 | Axe et al. | |
| 5,490,502 A | 2/1996 | Rapoport et al. | |
| 5,492,113 A | 2/1996 | Estes et al. | |
| 5,515,844 A * | 5/1996 | Chirstopher | 128/200.26 |
| 5,522,382 A * | 6/1996 | Sullivan et al. | 128/204.23 |
| RE35,295 E | 7/1996 | Estes et al. | |
| 5,535,738 A | 7/1996 | Estes et al. | |
| 5,540,219 A | 7/1996 | Mechlenburg et al. | |
| 5,544,648 A * | 8/1996 | Fischer, Jr. | 128/207.14 |
| 5,546,935 A * | 8/1996 | Champeau | 128/205.23 |
| 5,551,419 A * | 9/1996 | Froehlich et al. | 128/204.23 |
| 5,558,081 A | 9/1996 | Lipkin | |
| 5,606,968 A * | 3/1997 | Mang | 128/207.14 |
| 5,692,497 A * | 12/1997 | Schnitzer et al. | 128/204.21 |
| 5,704,345 A * | 1/1998 | Berthon-Jones | 128/204.23 |
| 5,711,296 A * | 1/1998 | Kolobow | 128/205.13 |
| 5,752,506 A * | 5/1998 | Richardson | 128/204.18 |
| 5,752,921 A * | 5/1998 | Orr | 600/533 |
| 5,896,854 A * | 4/1999 | Bliss et al. | 128/200.24 |
| 6,102,041 A * | 8/2000 | Boussignac et al. | 128/207.15 |
| 6,102,042 A * | 8/2000 | Hete et al. | 128/207.16 |
| 6,196,222 B1 * | 3/2001 | Heinonen et al. | 128/204.23 |

OTHER PUBLICATIONS

Murray et al., Textbook of Respiratory Medicine, 2nd ed. WB Sanders Co. pp. 2305–2306, Jul. 1994.*

Heimlich et al., "Transtracheal Catheter Technique For Plumonary Rehabilitation", *Ann. Otol. Rhinol. Laryngol.,* 1985, pp. 502–504, vol. 94.

Christopher et al., "A Program for Transtracheal Oxygen Delivery", *Annals of Internal Medicine,* 1987, pp. 802–808, vol. 107.

Couser, Jr. et al., "Transtracheal Oxygen Decreases Inspired Minute Ventilation", *Am. Rev. Respir. Dis.,* 1989, pp. 627–631, vol. 139.

Bloom et al., "Transtracheal Oxygen Delivery and Patients with Chronic Obstructive Pulmonary Disease", *Respiratory Medicine,* 1989, pp. 281–288, vol. 83.

O'Donohue, Jr., "Transtracheal Oxygen: A Step Beyond the Nasal Cannula for Long–Term Oxygen Therapy", *Nebraska Medical Journal,* Nov. 1992, pp. 291–295.

Hoffman et al., "Nasal Cannula and Transtracheal Oxygen Delivery", *Am. Rev. Respir. Dis.,* 1992, pp. 837–831, vol. 145.

Benditt et al., "Transtracheal Delivery of Gas Decreases the Oxygen Cost of Breathing", *Am. Rev. Respir. Dis.,* 1993, pp. 1207–1210, vol. 147.

Kribbs et al., "Objective Measurement of Patterns of Nasal CPAP Use by Patients with Obstructive Sleep Apnea", *Am. Rev. Respir. Dis.,* 1993, pp. 887–895, vol. 147.

Jones et al., "Nasal Pressure Support Ventilation Plus Oxygen Compared with Oxygen Therapy Alone in Hypercapnic COPD", *Am. J. Respir. Crit. Care Med.,* 1995, pp. 538–544, vol. 152.

American Thoracic Society, "Standards for the Diagnosis and Care of Patients with Chronic Obstructive Plumonary Disease", *Am. J. Respir. Crit. Car Med.,* 1995, pp. S77–S120, vol. 152.

Gay et al., "Efficacy of Nocturnal Nasal Ventilation in Stable, Severe Chronic Obstructive Pulmonary Disease During a 3–Month Controlled Trial", *Mayo Clin. Proc.,* Jun. 1996, pp. 533–542, vol. 71, No. 6.

Strohl, "The Biology of Sleep Apnea", *Science and Medicine,* Sep./Oct. 1996, pp. 32–41.

Schaten et al., "High–Flow Transtracheal Oxygen: A Promising Technique for the Management of Hypercarbic Respiratory Failure", *Abstracts,* p. 22S, 56th Annual Scientific Assembly.

* cited by examiner

METHOD AND APPARATUS FOR PROVIDING VENTILATORY SUPPORT TO A PATIENT

CROSS REFERENCE TO RELATED APPLICATION

This application claims the benefit of Provisional Application No. 60/033,322, filed Dec. 12, 1996, which is incorporated herein by reference.

FIELD OF THE INVENTION

The present invention relates to a ventilatory support system, and more particularly relates to a method and apparatus for providing a controlled flow of breathing gas to a patient based on the function of the patient's upper airways which vary over time in relation to the physiological requirements of the patient.

BACKGROUND INFORMATION

There are many clinical disorders that are characterized by the failure of patients to maintain adequate ventilation. In general, ventilation can be compromised in one of two ways. First, there are patients who cannot breathe adequately due to excessive mechanical loads on the ventilatory apparatus or weakness of the respiratory muscles. Examples of such mechanical loads include upper airway obstruction in obstructive sleep apnea, bronchial obstruction in asthma and chronic obstructive pulmonary disease, and reductions in lung or chest wall compliance in diseases involving the pulmonary parenchymal and chest wall. Second, ventilation may be compromised by a failure of neuromuscular mechanisms in patients who may have disorders involving the central nervous system or phrenic nerves. Regardless of etiology, each of these disorders is associated with reduced levels of ventilation.

In patients with reduced levels of ventilation, ventilation can be augmented by blowing air into the airway. In one approach, air can be applied to help wash $CO_2$ out from the airways. When an additional source of air is applied to the central airways, ventilation may fall because less is required to eliminate $CO_2$. Currently, two such methods are utilized clinically to aid $CO_2$ washout from the airways. In intubated patients, air is administered either continuously or during expiration by a process known as tracheal gas insufflation (TGI). Alternatively, air can be administered through a thin transtracheal cannula in non-intubated, spontaneously breathing patients. Current evidence suggests that low flow rates up to 5 to 6 liters/min can wash out $CO_2$ and reduce a patient's ventilatory requirements. For $CO_2$ washout to occur, insufflated air must vent freely to atmosphere. With continuous transtracheal insufflation (TTI), therefore, $CO_2$ washout allows patients to reduce ventilation without increasing $CO_2$.

In another approach, mechanical ventilation can be instituted to augment ventilation. Positive pressure ventilation is the most common form of mechanical ventilation. It is characterized by intermittent application of positive pressure to the airway. When airway pressure is increased, the lungs inflate. Deflation occurs passively after allowing the airway pressure to fall. Therefore, positive pressure can be applied intermittently to the airway to augment ventilation in patients who cannot maintain normal levels of ventilation on their own. Various mechanisms have been developed to augment ventilation with positive pressure devices, including endotracheal tubes, tracheostomy tubes and nasal/oronasal masks. In each example, a tight seal is required between the ventilator and the patient's airway, thereby preventing leakage of air when positive pressure is applied. As a result, these interfaces are relatively intrusive, and interfere with speech, swallowing, normal breathing patterns, and normal sleep/wake rhythms.

Obstructive sleep apnea is one example of a condition in which there is cyclic occlusion and reopening of the pharynx, which results in the obstruction of airflow during sleep, hypoxic episodes and daytime somnolence. Two general approaches have been utilized to treat this disorder. First, methods have been devised to relieve pharyngeal airflow obstruction. At present, nasal continuous positive airway pressure (nCPAP) is the most effective way to relieve obstruction. It is applied via a nasal mask and maintains pharyngeal patency during sleep. CPAP is most effective when a tight seal is maintained between the patient's airway and the nasal mask. U.S. Pat. Nos. 5,551,419, 5,540,219, Re. 35,295, 5,535,738, and 5,490,502 disclose the use of such CPAP devices. However, despite its low incidence of side effects CPAP is often not well tolerated, and many patients do not adhere to therapy because the tightly applied nasal mask causes claustrophobia (Kribbs et al., *Am. Rev. Respir. Dis.*, Vol. 147, 1993). The present invention, however, does not require such a tight seal. Rather than relieving upper airway obstruction as nasal CPAP, it works in concert with the patient's breathing efforts and the natural tendency of the upper airway to collapse and obstruct the exit of airflow from the lungs.

When relief of pharyngeal obstruction is not achievable with nasal CPAP, tracheostomy provides an alternative breathing route during sleep which bypasses the pharynx. It is effective in treating this disorder because it provides a widely patent bypass route for breathing. With tracheostomy, air can be inspired and expired freely from/to atmosphere irrespective of the state of the upper airway patency. Although highly effective in treating apneic patients, tracheostomy is associated with significant morbidity from repeated airway infections, intractable cough, speech difficulties and disfigurement. Because of its high morbidity, tracheostomy is rarely considered by either patients or physicians to be an acceptable therapeutic alternative, except when sleep apnea is life-threatening. The present invention avoids these adverse effects, yet provides a mechanism for both inspiration and expiration that utilizes the upper airway to coordinate the pattern of airflow.

Another proposed method is to provide long-term supplemental oxygen therapy via a thin transtracheal cannula through which a low flow rate of oxygen is delivered intratracheally to patients with lung disease. U.S. Pat. Nos. 5,181,509 and 5,090,408 disclose examples of such cannulas. Clinical reports and experience with this type of cannula has shown it to be an effective, well tolerated oxygen delivery method. However, the low flow rate of oxygen is not sufficient to provide satisfactory ventilatory support to patients.

U.S. Pat. Nos. 5,101,820 and 5,279,288 to Christopher disclose the use of a transtracheal catheter to provide a continuous high flow rate of oxygen-containing gas to a patient. However, there are disadvantages associated with the continuous delivery of gas to patients, such as spasm of the vocal cords and closure of the upper airway. This can result in the rapid buildup of excessive pressure in the trachea and lungs of the patient (pneumothorax and pneumomediastinum) and alterations in the breathing pattern which perpetuate problems with sleep disruption and daytime hypersomnolence.

The disclosure of each of the patents cited above is incorporated herein by reference.

The present invention has been developed in view of the foregoing and to overcome other deficiencies of the prior art.

SUMMARY OF THE INVENTION

The present invention provides a ventilatory support system which controls the flow of breathing gas to a patient based on the function of the patient's upper airway and his or her ventilatory needs. Gas pressure in the trachea of the patient is measured, and the delivery of breathing gas to the patient is controlled based on the sensed gas pressure. Depending on the upper airway function of the patient, a tracheal gas pressure limit and a breathing gas flow rate value are established. When the tracheal gas pressure limit is reached, the flow of breathing gas is reduced or terminated. The flow of breathing gas is subsequently resumed either immediately, after a delay period, or after the tracheal gas pressure falls to a predetermined level. The system thus provides a feedback loop using tracheal pressure which reflects a patient's ventilatory and upper airway status in order to control the flow of breathing gas.

An important feature of the present invention is that the upper airways of the patient constitute an integral part of the breathing circuit. The upper airways serve as a valve which controls whether the applied tracheal breathing gas inflates the lungs or vents to atmosphere. We have recognized that the upper airways obstruct flow progressively as the tracheal pressure falls toward and below a critical pressure ($P_{CRIT}$). As the upper airway obstructs progressively, more and more of the applied flow is directed toward and inflates the lungs. Under these circumstances, a greater proportion of the breathing gas supplied by the device is used to satisfy his or her ventilatory demand. On the other hand, any increase in tracheal pressure above this critical pressure facilitates exhalation of breathing gas and $CO_2$ washout from anatomic dead space. A major advantage of the invention is that it can maintain tracheal pressure in a range which optimizes delivery of inspired gas to the lungs and facilitates venting of exhaled gas through the upper airways.

The system of the present invention is useful in treating many different types of clinical disorders. For example, the system may be used to treat patients with upper airway obstruction, such as patients suffering from obstructive sleep apnea. The present system may be used to treat such patients by maintaining tracheal gas pressure above a critical level so as to provide sufficient air to inspire, yet allow free release of air through the upper airways during expiration. Similar mechanisms can be utilized to augment both ventilation and $CO_2$ washout in patients with other breathing disorders, even when upper airway obstruction is absent.

In a preferred embodiment, treatment with the system of the present invention is associated with alternate opening and with partial or complete closing of the upper airway of the patient. Depending on the level of the patient's tracheal pressure, the upper airway can be either open or closed to atmosphere. The system of the present invention controls the flow of breathing gas that it supplies to the lungs in concert with the patient's breathing efforts, and as a function of the patient's tracheal pressure. When tracheal pressure decreases, the upper airway progressively closes, thereby directing the flow of breathing gas toward the lungs. In contrast, when tracheal pressure increases during expiration, the upper airway progressively opens and exhaled gas is vented. The present invention interacts with the patient in such a way as to coordinate the delivery of flow to the trachea with both the patient's breathing demand and state of upper airway patency.

An object of the present invention is to provide a method for giving interactive ventilatory support to a patient based on the patient's ventilatory requirements and on the properties of the upper airways. A controlled flow of breathing gas is delivered to the patient based on the gas pressure in the trachea of the patient.

Another object of the present invention is to provide a method for supplying breathing gas to a patient including the steps of inserting a catheter into the trachea of a patient, establishing a tracheal gas pressure limit for the patient, measuring gas pressure in the trachea, and controlling the flow of breathing gas through the catheter based on the measured gas pressure in the trachea and the properties of the upper airways. The catheter is preferably inserted transtracheally. A breathing gas flow rate value is preferably established for the patient depending upon the upper airway properties and degree of ventilatory support required by the patient.

Another object of the present invention is to provide an apparatus for supplying breathing gas to a patient. The apparatus includes means for delivering breathing gas into the trachea of the patient, means for measuring gas pressure in the trachea, and means for controlling the flow of the breathing gas through the breathing gas delivery means into the trachea based on the measured gas pressure in the trachea.

Another object of the present invention is to provide an apparatus for supplying breathing gas to a patient including a source of breathing gas, a catheter in communication with the source of breathing gas, a tracheal pressure sensor for measuring gas pressure in the trachea of the patient, and a breathing gas flow controller connected to the source of breathing gas and the tracheal pressure sensor for controlling the flow of breathing gas.

These and other objects of the present invention will be more apparent from the following description.

DETAILED DESCRIPTION OF THE PREFERRED EMBODIMENTS

The method and apparatus of the present invention provide breathing gas to a patient based on the particular needs of the patient and the upper airway properties of the patient. As used herein, the term "patient" means members of the animal kingdom, including mammals such as humans. The term "breathing gas" as used herein means an oxygen-containing gas, such as air, air supplemented with additional oxygen and/or medications, substantially pure oxygen, and the like. The breathing gas may optionally be humidified and/or heated to approximately the same temperature as the body temperature of the patient being treated. Furthermore, the breathing gas may optionally include other components such as anesthesia, pharmalogic agents administered by continuous or intermittent dosing schedules, and components for augmentation of speech/voice volume.

In accordance with the present invention, a tracheal gas pressure limit ($P_{LIM}$) is established for the patient to be treated. In the preferred embodiment, a breathing gas flow rate value ($\dot{V}_{IN}$) is also established for the patient. When gas pressure in the trachea ($P_{TRACH}$) of the patient is below $P_{LIM}$, breathing gas is delivered to the trachea of the patient at the established breathing gas flow rate value $\dot{V}_{IN}$. However, when the tracheal pressure $P_{TRACH}$ of the patient exceeds $P_{LIM}$, the flow of breathing gas is reduced or terminated. The flow of breathing gas is then resumed at the flow rate value $\dot{V}_{IN}$, which may be resumed immediately, after a delay period, or after the tracheal pressure falls to a predetermined value. In the preferred embodiment, the flow of breathing gas is provided transtracheally to the patient, and is referred to herein as transtracheal insufflation (TTI).

Figure 1:
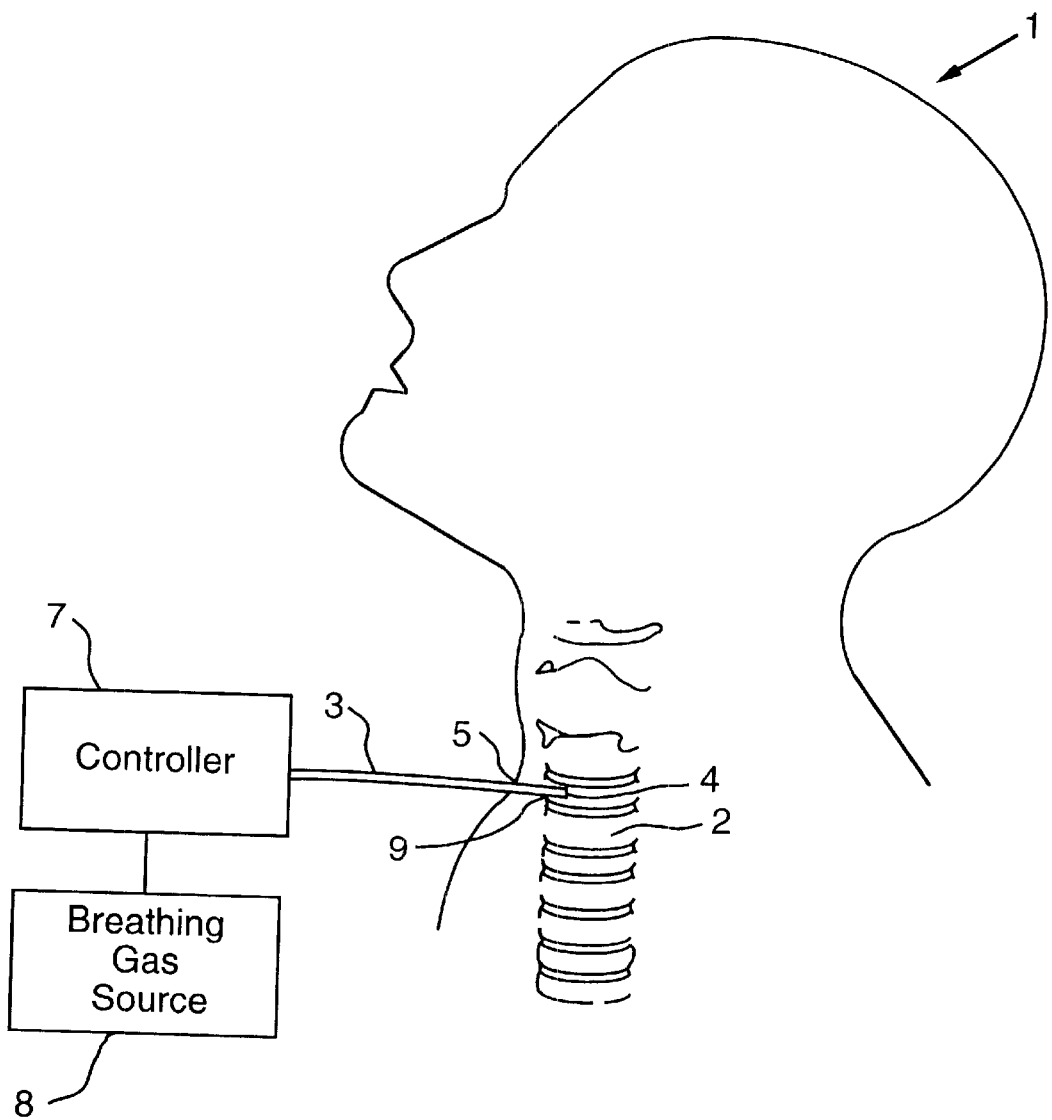
FIG. 1 is a schematic illustration showing the treatment of an obstructive sleep apnea patient with a ventilatory support system in accordance with an embodiment of the present invention.

FIG. 1 schematically illustrates a ventilatory support system used with a patient 1 in accordance with an embodiment of the present invention. The trachea 2 of the patient 1 is provided with an inflow of breathing gas by means of a catheter 3. The catheter 3 includes a distal end 4 which is inserted through an incision 5 in the throat of the patient 1 into the trachea 2. A controller 7 is connected to the catheter 3 for controlling the supply of breathing gas from a breathing gas source 8. A pressure sensor 9 measures gas pressure in the trachea 2 and supplies signals corresponding to the measured tracheal gas pressure to the controller 7. The pressure sensor 9 is located near the distal end 4 of the catheter 3 or, alternatively, contained within the controller 7 and connected to the trachea 2 by a cannula. As more fully described below, the controller 7 receives signals from the tracheal pressure sensor 9, and controls the flow of breathing gas from the breathing gas source 8 through the catheter 3 into the trachea 2. While a transtracheal catheter 3 is shown in FIG. 1, and is primarily described herein, it is to be understood that other types of catheters may be used in accordance with the present invention, such as catheters inserted into the trachea via the upper airway of the patient. The term "trachea" is used broadly herein to include any portion of a patient's airway from the carina to the nasal or mouth opening, preferably from the carina to the pharyngeal airway, most preferably below the vocal cords.

Depending on the pressure $P_{TRACH}$ measured by the tracheal pressure sensor 9, the breathing gas is either: (1) delivered through the catheter 3 at the established breathing gas flow rate value $\dot{V}_{IN}$ when tracheal pressure $P_{TRACH}$ is below the tracheal gas pressure limit $P_{LIM}$; or (2) terminated or delivered at a reduced flow rate below $\dot{V}_{IN}$ when the tracheal gas pressure limit $P_{LIM}$ is reached. If $\dot{V}_{IN}$ is reduced and $P_{TRACH}$ continues to rise, $\dot{V}_{IN}$ is preferably cut-off if pressure rises to a maximum limit ($P_{MAX}$). The breathing gas flow rate value $\dot{V}_{IN}$ is typically established at a substantially constant level for many patients, usually from about 4 to about 60 liters/minute, preferably from about 8 to about 50 liters/minute, depending on the particular physiological requirements of the patient. Once the measured gas pressure in the trachea $P_{TRACH}$ reaches the tracheal gas pressure limit $P_{LIM}$, the inflow of breathing gas is reduced below the breathing gas flow rate value $\dot{V}_{IN}$, preferably to a level of from 0 to about 20 percent of the breathing gas flow rate value $\dot{V}_{IN}$. For many patients, it may be preferable to fully terminate the flow of breathing gas when the measured tracheal gas pressure $P_{TRACH}$ reaches the tracheal gas pressure limit $P_{LIM}$.

As more fully described below, the tracheal gas pressure limit $P_{LIM}$ of a particular patient is preferably established above a critical tracheal gas pressure level ($P_{CRIT}$) of the patient. As used herein, the term "critical tracheal gas pressure level" means the tracheal pressure level below which the airway of the patient becomes closed or obstructed. The following values of $P_{CRIT}$ represent typical ranges during sleep. For example, in patients suffering from obstructive sleep apnea, the critical tracheal gas pressure level $P_{CRIT}$ may typically range from about 0 cmH$_2$O to about 15 cmH$_2$O above atmospheric pressure. Patients with a variant known as obstructive hypopneas or upper airway resistance syndrome have a $P_{CRIT}$ of from about −5 cmH$_2$O to about 0 cmH$_2$O relative to atmospheric pressure. Patients who snore during sleep but have little apnea or hypopnea may have a typical critical tracheal gas pressure level of from about −10 to about −5 cmH$_2$O relative to atmospheric pressure, while patients undergoing normal breathing routines may have a typical critical tracheal gas pressure level of from about −20 to about −10 cmH$_2$O relative to atmospheric pressure. In contrast, $P_{CRIT}$ is usually below −30 cmH$_2$O relative to atmospheric pressure during wakefulness for most patients. However, in patients suffering from laryngeal dysfunction $P_{CRIT}$ may be from about −5 cmH$_2$O to about 5 cmH$_2$O relative to atmospheric pressure.

In a preferred embodiment of the present invention, the tracheal gas pressure limit $P_{LIM}$ is established above the critical tracheal gas pressure level $P_{CRIT}$ of the patient, typically from about 1 to about 30 cmH$_2$O above the critical tracheal gas pressure level $P_{CRIT}$, preferably from about 5 to about 20 cmH$_2$O above $P_{CRIT}$.

As an added safety feature, a maximum tracheal gas pressure value ($P_{MAX}$) may be established for the patient. If tracheal gas pressure reaches the maximum value $P_{MAX}$, the flow of breathing gas is automatically terminated in order to reduce the likelihood of injury to the patient. A suitable sensor device or controller may be used to quickly terminate the flow of breathing gas when the maximum tracheal gas pressure value is reached.

Under normal circumstances, upper airway patency is determined by the critical pressure $P_{CRIT}$. The $P_{CRIT}$ is associated with airway occlusion when it is positive relative to atmospheric intraluminal pressure, or patent upper airways when $P_{CRIT}$ is negative. Thus, alternations in upper airway patency are associated with corresponding changes in $P_{CRIT}$.

Figure 3:
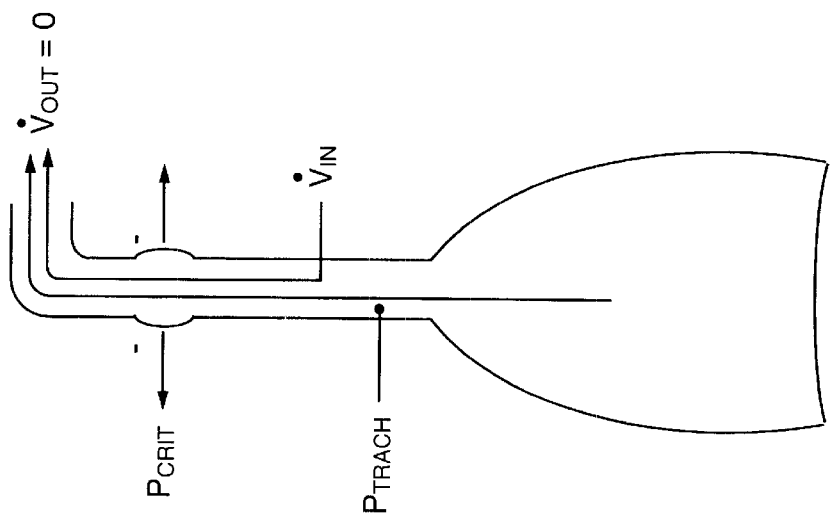
FIG. 3 is a schematic illustration showing the direction of an insufflation airstream when the upper airway is patent.
Figure 2:
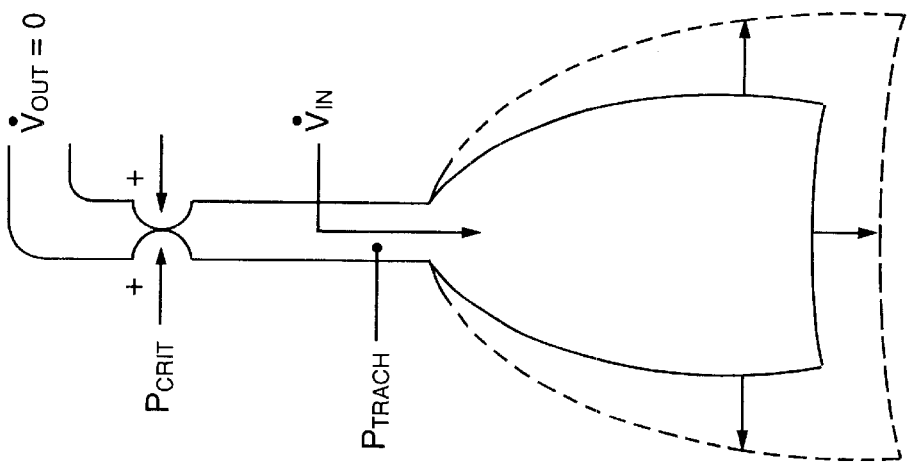
FIG. 2 is a schematic illustration showing the direction of an insufflation airstream when the upper airway is closed.

When air is applied to the trachea via transtracheal insufflation catheters, it can either vent through the upper airways or fill the lungs. The distribution of airflow between the upper airways and the lungs will therefore depend on the biomechanical properties of both the upper airways and respiratory system. As shown in FIG. 3, when the upper airways are widely patent, nearly all the air will vent out. Under these circumstances, $CO_2$ washout will be enhanced, but the patient's own level of ventilation will not be augmented. In contrast, as shown in FIG. 2, a severely narrowed or closed upper airway will direct nearly all the insufflation airstream into the lungs. The increase in lung inflation that results may augment ventilation, though $CO_2$ washout may not be enhanced. Thus, transtracheal insufflation will either augment $CO_2$ washout, or inflate the lungs, depending on the patency of the upper airways.

Figure 4:
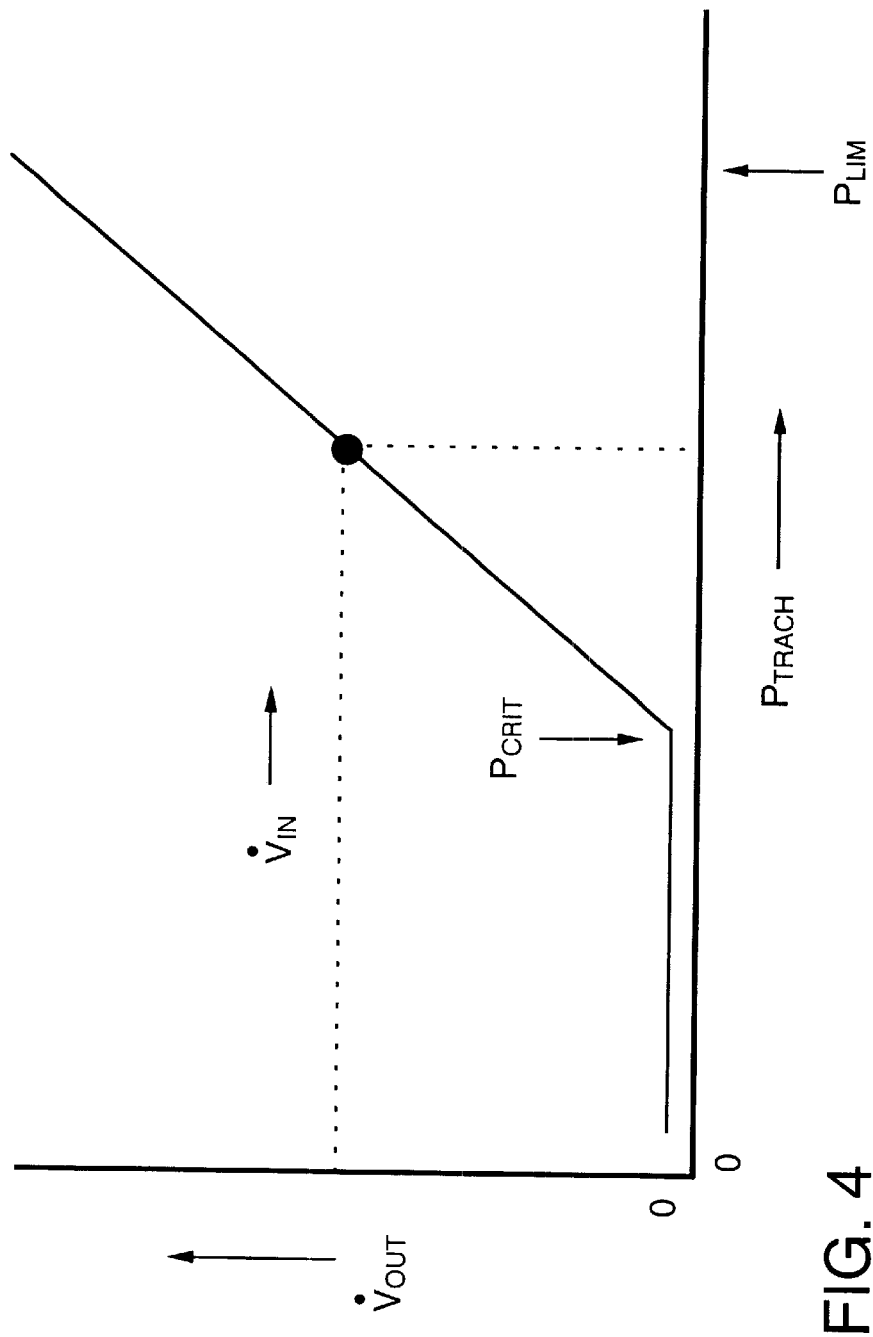
FIG. 4 is a graph illustrating the gas flow rate out of an obstructive sleep apnea patient's upper airways versus the gas pressure in the trachea of the patient.

FIG. 4 is a graph of the gas flow rate that vents out a patient's upper airways ($\dot{V}_{OUT}$) versus gas pressure in the trachea ($P_{TRACH}$) of the patient. When $P_{CRIT}$ is positive, the airway will remain closed until tracheal pressure exceeds $P_{CRIT}$. When tracheal pressure is less than $P_{CRIT}$, transtracheal insufflation will lead to a steady rise in intratracheal pressure $P_{TRACH}$ because air cannot vent through the upper airways ($\dot{V}_{OUT}$=0). This is illustrated by the flat portion of the graph shown in FIG. 4. This rise in $P_{TRACH}$ will be determined by the compliance of the respiratory system (lungs and chest wall, $C_{RS}$) and by the volume administered:

$$P_{TRACH}=(\dot{V}_{IN}\cdot \Delta t)/C_{RS}$$

where $\dot{V}_{IN}\cdot \Delta t$ represents the product of the insufflation flow $\dot{V}_{IN}$ over a given time. Once tracheal pressure $P_{TRACH}$ exceeds $P_{CRIT}$, shown by the inflection point in the graph of FIG. 4, air will begin to vent through the upper airways. At this stage, the relation between $\dot{V}_{OUT}$ and $P_{TRACH}$ is defined as:

$$\dot{V}_{OUT}=(P_{TRACH}-P_{CRIT})/R_s$$

where $R_s$ is the resistance of the tracheal airway segment between the insufflation site in the trachea and the site of upper airway collapse.

The tracheal pressure will then plateau at a level determined by the insufflation flow rate $\dot{V}_{IN}$ and by $P_{CRIT}$ as follows:

$$P_{TRACH} = (\dot{V}_{IN} \cdot R_s) + P_{CRIT}.$$

This equation describes the equilibrium position shown in FIG. 4 when $\dot{V}_{IN}$ is matched by $\dot{V}_{OUT}$ and the lungs are neither inflating nor deflating. For a given level of $\dot{V}_{IN}$, therefore, transtracheal insufflation leads to progressive lung inflation without $CO_2$ washout when $P_{TRACH}$ is less than $P_{CRIT}$. As $P_{TRACH}$ rises above $P_{CRIT}$, however, a new steady state of lung inflation with $CO_2$ washout is established. When a constant level of transtracheal insufflation is applied, therefore, the resting lung volume will increase by an amount that will be determined by $\dot{V}_{IN}$ and by the properties of the upper airways ($P_{CRIT}$ and $R_s$).

When $P_{CRIT}$ is negative, the response to transtracheal insufflation is analogous to the condition when $P_{TRACH}$ exceeds $P_{CRIT}$ above. With a negative $P_{CRIT}$, the upper airways remain patent, allowing air to vent out the upper airways continuously, as illustrated in FIG. 3. Under these circumstances, $P_{TRACH}$ will rise as determined by the level of $\dot{V}_{IN}$ and by the resistance of the entire upper airway, $R_{UA}$, as follows:

$$P_{TRACH} = \dot{V}_{IN} \cdot R_{UA}$$

For a given level of $\dot{V}_{IN}$, $P_{TRACH}$ will rise above atmospheric until a new steady state of lung inflation is established by the outflow resistance of the upper airways and $CO_2$ washout will occur.

The influence of a constant rate of transtracheal insufflation in the absence of any spontaneous breathing efforts has been considered above. The foregoing indicates that tracheal pressure will progressively rise and plateau at a defined level that exceeds either the upper airway $P_{CRIT}$ or atmospheric pressure (in the case of a negative $P_{CRIT}$). As the tracheal pressure rises, the lungs will inflate until a new steady state of lung inflation and $P_{TRACH}$ is achieved. At this level of $P_{TRACH}$, flow will leak out the upper airways, $\dot{V}_{OUT}$, at exactly the rate at which it is applied $\dot{V}_{IN}$. This leak flow will augment $CO_2$ washout from dead space, but will not augment ventilation or produce any bulk flow of gas into or out of the lungs. To augment ventilation, bulk flow of air in and out of the lungs is required.

Figure 5:
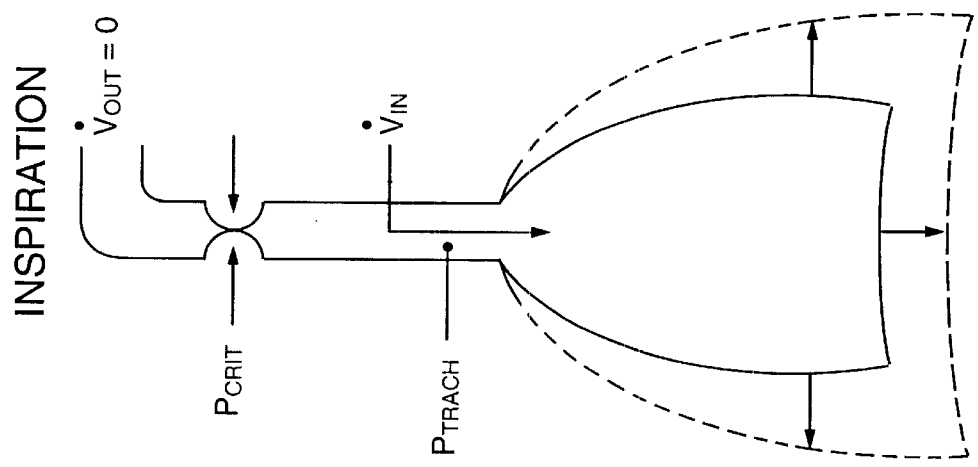
FIG. 5 is a schematic illustration showing the direction of an insufflation airstream during an inspiratory phase in an apneic patient with a positive critical pressure ($P_{CRIT}$) during sleep.

Spontaneous breathing efforts can produce such bulk flow by creating pressure gradients along the tracheobronchial tree that propel air in and out of the lungs. During the inspiratory phase, $P_{TRACH}$ falls, leading to an inflow of breathing gas from the $\dot{V}_{IN}$ source into the lungs, as shown in FIG. 5. In contrast to the steady state condition in which $\dot{V}_{IN}$ and $\dot{V}_{OUT}$ are equal, $\dot{V}_{OUT}$ now diminishes by the amount of $\dot{V}_{IN}$ that is diverted to the lungs. As $P_{TRACH}$ falls during inspiration, the upper airways progressively obstruct, allowing less flow to vent to atmosphere. When the patient's inspiratory flow requirement is less than $\dot{V}_{IN}$, some insufflated gas continues to vent out ($\dot{V}_{OUT}$ remains >0) and the upper airway remains partially open. If the patient's inspiratory flow demand is greater than $\dot{V}_{IN}$, however, $P_{TRACH}$ will fall below $P_{CRIT}$ and the upper airway will close. Thereafter, all $\dot{V}_{IN}$ will be diverted to the lungs. Thus, inspiratory decreases in $P_{TRACH}$ during spontaneous breathing produce alterations in upper airway patency that control the amount of $\dot{V}_{IN}$ that inflates the lungs or leaks out the upper airways (FIG. 5).

The foregoing also indicates that $\dot{V}_{IN}$ is the sole source of inspired flow when the upper airway $P_{CRIT}$ is positive. Therefore, sufficient $\dot{V}_{IN}$ must be provided to the spontaneously breathing patient to meet his or her flow requirement, particularly when the upper airway $P_{CRIT}$ is positive (as it is in patients with obstructive sleep apnea). Under these circumstances, $\dot{V}_{IN}$ in the range of about 300–600 ml/s (18–36 liters/min) is usually required to match peak inspiratory flow demands during sleep. Alternatively, a $\dot{V}_{IN}$ of about 150–300 ml/s (9–18 liters/min.) is usually all that is required to meet mean inspiratory flow requirements during sleep. When peak flow demands are not matched, however, tracheal pressure will fall substantially during inspiration. Therefore, the magnitude of the fall in tracheal pressure during inspiration can be utilized to gauge how well $\dot{V}_{IN}$ is meeting the patient's inspiratory flow requirements is satisfied by the level of $\dot{V}_{IN}$.

Figure 6:
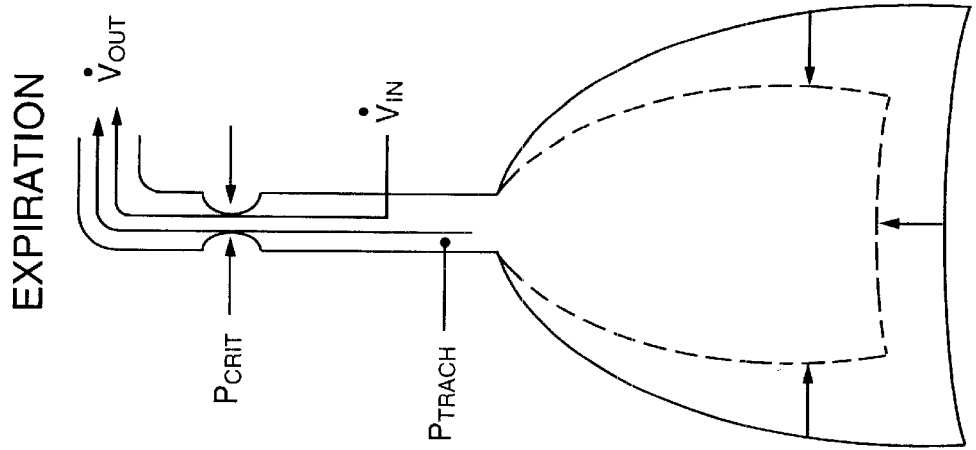
FIG. 6 is a schematic illustration showing the direction of an insufflation airstream during an expiratory phase in an apneic patient with a positive critical pressure ($P_{CRIT}$) during sleep.

During expiration, tracheal pressure rises. As it rises above $P_{CRIT}$, outgoing flow is generated through the upper airways as shown in the graph in FIG. 4 and illustrated in FIG. 6. Under these circumstances, insufflated gas, $\dot{V}_{IN}$, is added to the exhaled gas stream, thereby increasing the washout of $CO_2$ from the central airways. TTI administration during expiration, therefore, helps increase $CO_2$ washout from the respiratory system.

From the foregoing, it is evident that TTI works in concert with the patient's upper airway to regulate breathing patterns throughout the respiratory cycle. The patient's upper airway works to either maximize the delivery of breathing gas ($\dot{V}_{IN}$) to the lungs during inspiration when tracheal pressure falls, or to vent exhaled gas from the lungs and TTI source during expiration when tracheal pressure rises. Such differences in upper airway function between inspiration and expiration are produced by fluctuations in tracheal pressure which are in turn determined by the balance between the patient's breathing effort and the $\dot{V}_{IN}$ level. A marked fall in tracheal pressure during inspiration indicates that greater levels of $\dot{V}_{IN}$ should be applied to meet the patient's ventilatory demands. In contrast, a marked rise in tracheal pressure during expiration will be associated with greater levels of $CO_2$ washout through the upper airways which could be curtailed by either stopping $\dot{V}_{IN}$ or reducing the $\dot{V}_{IN}$ level. Thus, TTI gas delivery to the lungs and $CO_2$ washout from the lungs are maximized when inspiratory and expiratory tracheal pressure swings are large, respectively.

In the preferred embodiment of the present invention, the tracheal pressure signal is utilized to provide for separate adjustment of the level of TTI gas delivery to the lungs during inspiration and $CO_2$ washout from the respiratory system during expiration. Such adjustment is accomplished with two settings in accordance with the invention. First, the $\dot{V}_{IN}$ level is set to provide inspiratory flow as desired. Second, a level of tracheal pressure is determined, above which $\dot{V}_{IN}$ is either curtailed or cut off. This tracheal pressure limit, $P_{LIM}$, is preferably set above the upper airway $P_{CRIT}$, so that air can vent freely out the upper airways whenever tracheal pressure rises above $P_{CRIT}$. Nevertheless, $P_{LIM}$ will limit $CO_2$ washout whenever the level of $\dot{V}_{IN}$ is sufficiently high that $P_{TRACH}$ rises to $P_{LIM}$ during expiration. Thus, $\dot{V}_{IN}$ and $P_{LIM}$ can be individually adjusted to meet patient needs for inspiratory flow and $CO_2$ washout, respectively.

The pattern of TTI administration will also vary depending on the particular level of $\dot{V}_{IN}$ and $P_{LIM}$ set. Depending on where $P_{LIM}$ is set relative to the tracheal pressure at $\dot{V}_{IN}$ (see point on graph at $\dot{V}_{IN}$ level, FIG. 4), insufflation will be continuous (when $P_{LIM}$ is significantly higher than $P_{TRACH}$ at a given $\dot{V}_{IN}$) or intermittent (when $P_{LIM}$ is only slightly higher or even lower than $P_{TRACH}$ at a given $\dot{V}_{IN}$). When intermittent flow occurs in concert with spontaneous breathing efforts ($P_{TRACH}$ falls from the point on the graph, FIG. 4), the insufflation flow $\dot{V}_{IN}$, assists the delivery of airflow to the lungs. This pattern of intermittent transtracheal insufflation that is coordinated with active (spontaneous) breathing efforts is referred to herein as active transtracheal insufflation (ATTI).

When spontaneous breathing efforts are absent, another type of intermittent flow regimen is possible. In this embodiment, tracheal pressure is maintained at a relatively high level by the use of relatively high levels of $\dot{V}_{IN}$, and by setting $P_{LIM}$ at a relatively high value. At these high levels of $\dot{V}_{IN}$ and $P_{LIM}$, spontaneous breathing efforts often extinguish, particularly in the transitional sleep stage, as more fully described below. Exhalation of gas from the lungs is accomplished by intermittently reducing or terminating $\dot{V}_{IN}$, allowing $P_{TRACH}$ to fall as the lungs deflate. After a specified delay time, or after a specified differential tracheal pressure level is reached, $\dot{V}_{IN}$ resumes. This pattern of intermittent insufflation in the absence of spontaneous breathing efforts is referred to herein as passive transtracheal insufflation (PTTI) because the respiratory system is being passively inflated and deflated.

Depending on the physiologic needs of a particular patient and his or her upper airway properties, the method and apparatus of the present invention may function in both continuous and intermittent modes, and in combinations of both the intermittent ATTI and PTTI modes. These distinct breathing patterns and modes of ventilatory support result from setting specific $\dot{V}_{IN}$ and $P_{LIM}$ levels relative to the upper airway $P_{CRIT}$ and pressure-flow relationships (FIG. 4).

With either the continuous or the intermittent ATTI modes, $\dot{V}_{IN}$ may not be sufficient to meet the patient's ventilatory demands, as noted above. In this case, $P_{TRACH}$ will fall progressively during inspiration in the spontaneously breathing patient. When such falls in $P_{TRACH}$ are observed, the $\dot{V}_{IN}$ level may then be increased to provide the required additional inspiratory flow, as described more fully below.

In the intermittent PTTI embodiment, breathing gas will initially flow continuously through the trachea and vent out the upper airways. Bulk flow of air in and out of the lungs will not occur until $\dot{V}_{IN}$ is turned on and off or varied so as to intermittently inflate and deflate the lungs. As the lungs deflate, air will only vent freely through the upper airways as long as $P_{TRACH}$ remains above the upper airway $P_{CRIT}$ The $\dot{V}_{IN}$ level will be therefore cycled on and off to provide rhythmic inflation and deflation, and to maintain adequate tidal volumes and minute ventilation.

Figure 7:
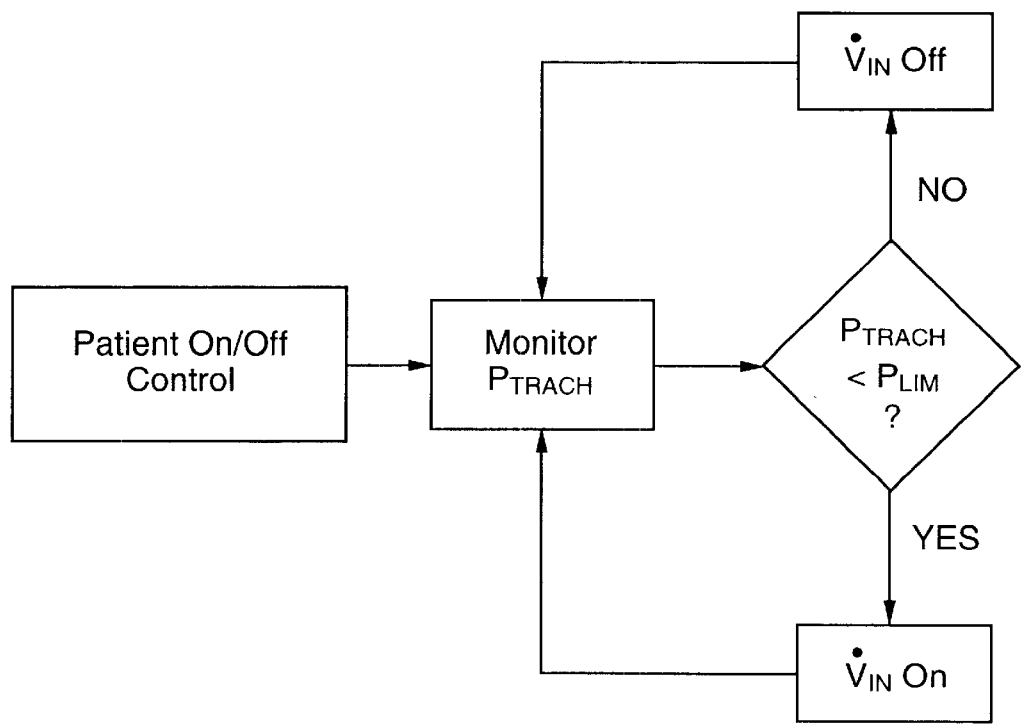
FIG. 7 is a schematic diagram showing an algorithm for controlling the flow of breathing gas to a patient in accordance with an embodiment of the present invention.
Figure 8:
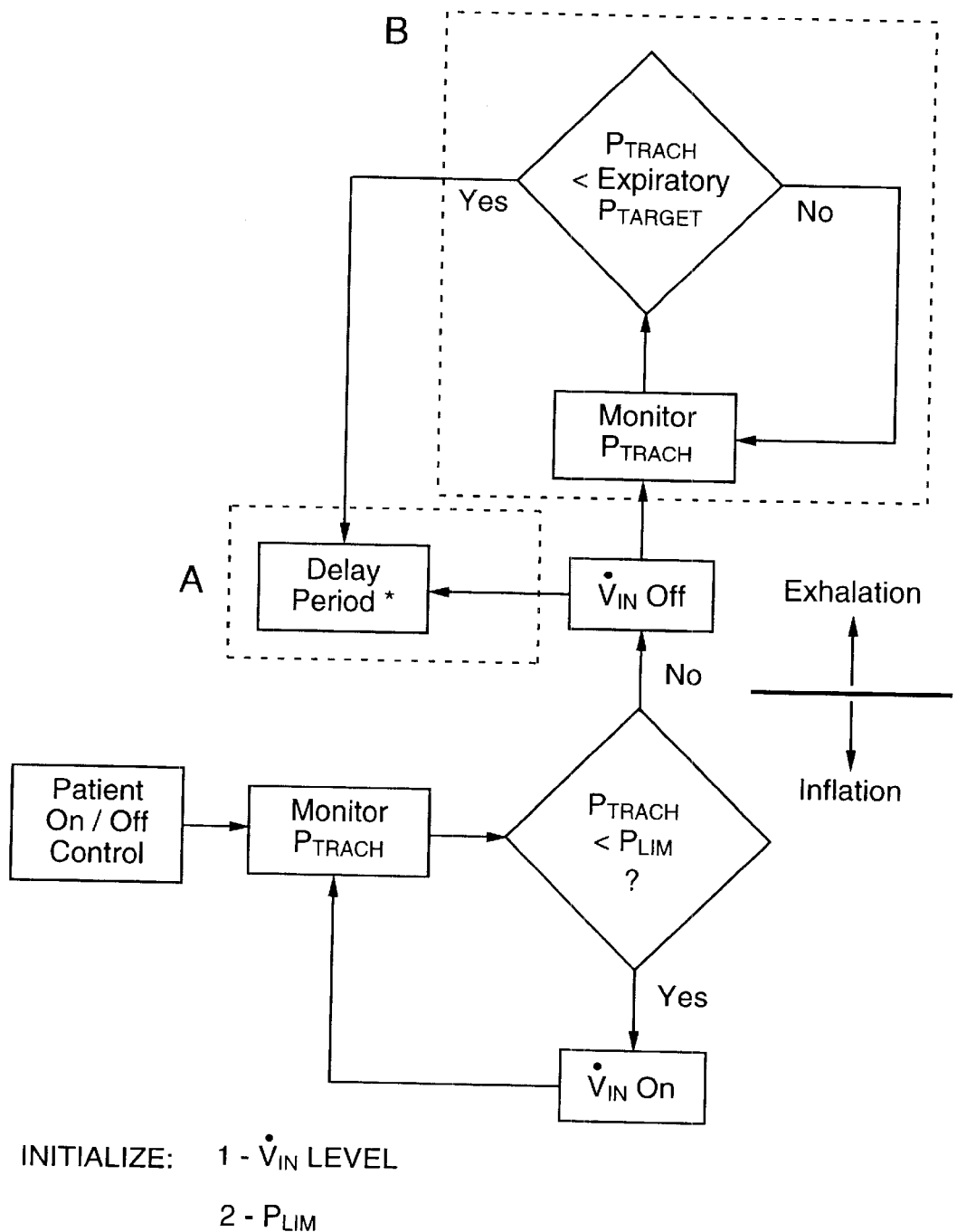
FIG. 8 is a schematic diagram showing an algorithm for controlling the flow of breathing gas to a patient in accordance with embodiments of the present invention.

FIGS. 7 and 8 are schematic diagrams illustrating algorithms in accordance with various embodiments of the present invention. FIG. 7 shows the continuous and the intermittent ATTI embodiment of the present invention. In this mode, $\dot{V}_{IN}$ and $P_{LIM}$ are initialized to threshold values by a titration protocol, as more fully described below. $P_{TRACH}$ is then monitored. If the measured tracheal pressure is less than $P_{LIM}$, $\dot{V}_{IN}$ is on, but if $P_{TRACH}$ rises above $P_{LIM}$, $\dot{V}_{IN}$ is turned off or reduced.

The intermittent PTTI mode is included in the schematic diagram of FIG. 8, which adds additional capabilities to the schematic shown in FIG. 7. In this embodiment, $\dot{V}_{In}$ and $P_{LIM}$ are initialized as before. A delay period may also be set, for example, to 0 when continuous or intermittent insufflation is prescribed for a spontaneously breathing patient, or to a specified amount (e.g., 0.5 to 6 seconds) for patients who are not spontaneously breathing. The use of a delay period is illustrated in box A in FIG. 8. Alternatively, as shown in box B of FIG. 8, an expiratory target tracheal pressure, $P_{TARGET}$, may be set less than $P_{LIM}$. If $P_{TRACH}$ is less than $P_{TARGET}$, $\dot{V}_{IN}$ will be turned on and will continue until $P_{TRACH}$ reaches $P_{LIM}$. If $P_{TRACH}$ is greater than $P_{TARGET}$, $\dot{V}$ will not be resumed until $P_{TRACH}$ falls below $P_{TARGET}$.

In accordance with the PTTI embodiment of the present invention, if $\dot{V}_{IN}$ is set at about 15–45 liters/min. and $P_{LIM}$ is set at approximately 30 cmH$_2$O, constant insufflation typically results during sleep. A $P_{LIM}$ is also set such that $\dot{V}_{IN}$ is started when $P_{TRACH}$ falls below $P_{LIM}$. In this case, when $P_{TRACH}$ exceeds $P_{LIM}$, $\dot{V}_{IN}$ is turned off (or diverted to atmosphere) or lowered. $\dot{V}_{IN}$ may then be resumed after a set delay period, e.g., 0.5 to 6 seconds (preferably from about 1 to about 4 seconds for many patients), during which time the lungs deflate. Alternatively, $P_{TRACH}$ may be allowed to decay to a prescribed expiratory target $P_{TARGET}$ before $\dot{V}_{IN}$ is resumed.

In PTTI, the time constant ($\tau$) of this response may be determined by the upper airway resistance ($R_S$ for obstructive sleep apneic patients, $R_{US}$ for unobstructed non-apneic patients) and respiratory system compliance ($\tau = 1/(R_S \cdot C_{rs})$), and the $P_{TRACH}$ asymptotes at the upper airway $P_{CRIT}$ or atmospheric, respectively. In typical patients with obstructive sleep apnea, a $\dot{V}_{IN}$ of about 15 liters/min produces inflation/deflation swings in $P_{TRACH}$ of about 5–10 cmH$_2$O in 1–3 seconds, and is associated with adequate ventilation.

Alternatively, the flow of breathing gas may be resumed when the measured gas pressure in the trachea falls to a differential tracheal gas pressure level ($P_{TARGET}$) below the tracheal gas pressure limit $P_{LIM}$. In this embodiment, the differential tracheal gas pressure level $P_{TARGET}$ is typically from about 2 to about 40 cmH$_2$O below the tracheal gas pressure limit $P_{LIM}$, preferably from about 3 to about 15 cmH$_2$O below $P_{LIM}$.

Figure 9:
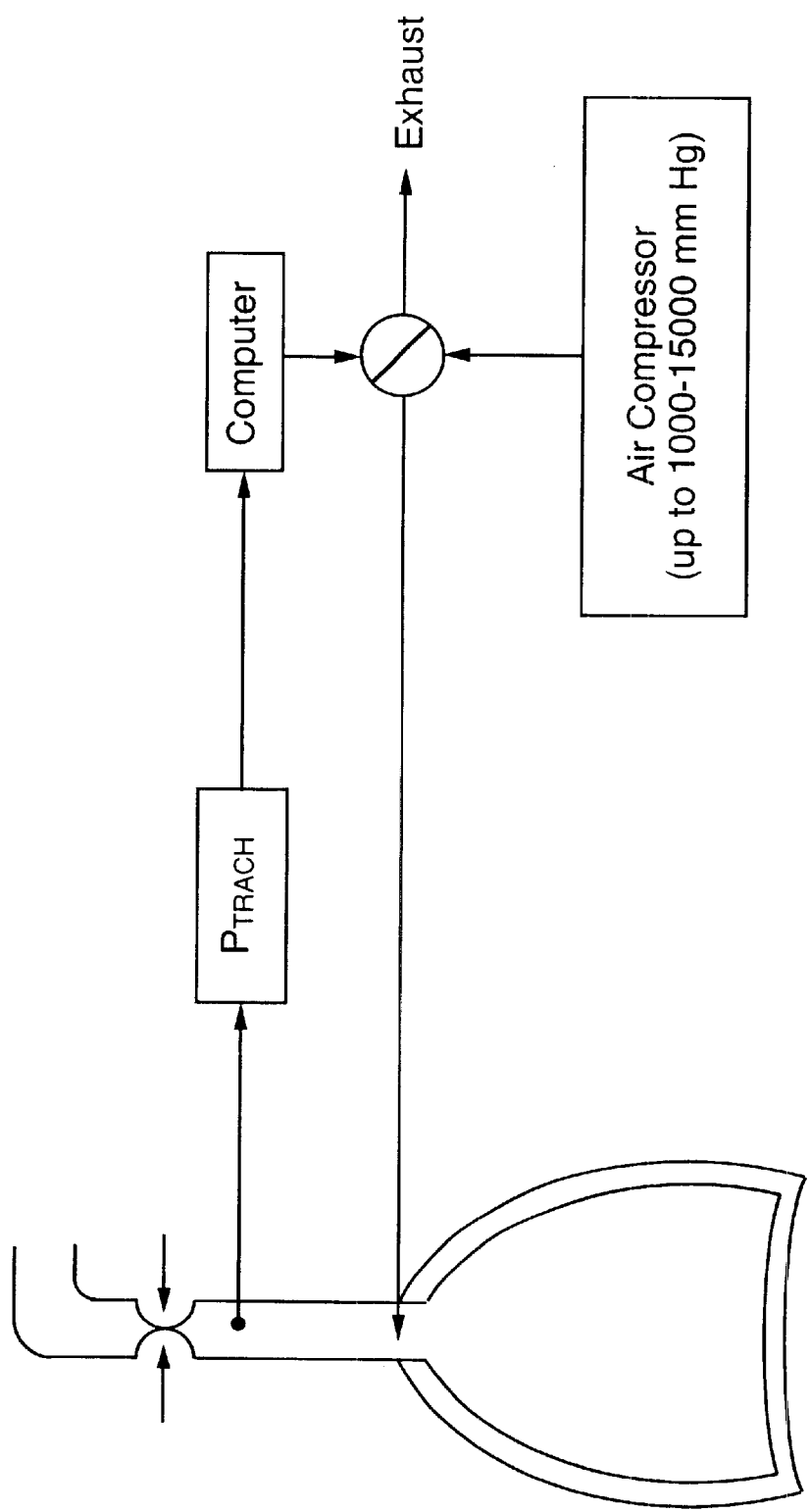
FIG. 9 is a schematic illustration of an apparatus provided in accordance with an exemplary embodiment of the present invention.
Figure 10:
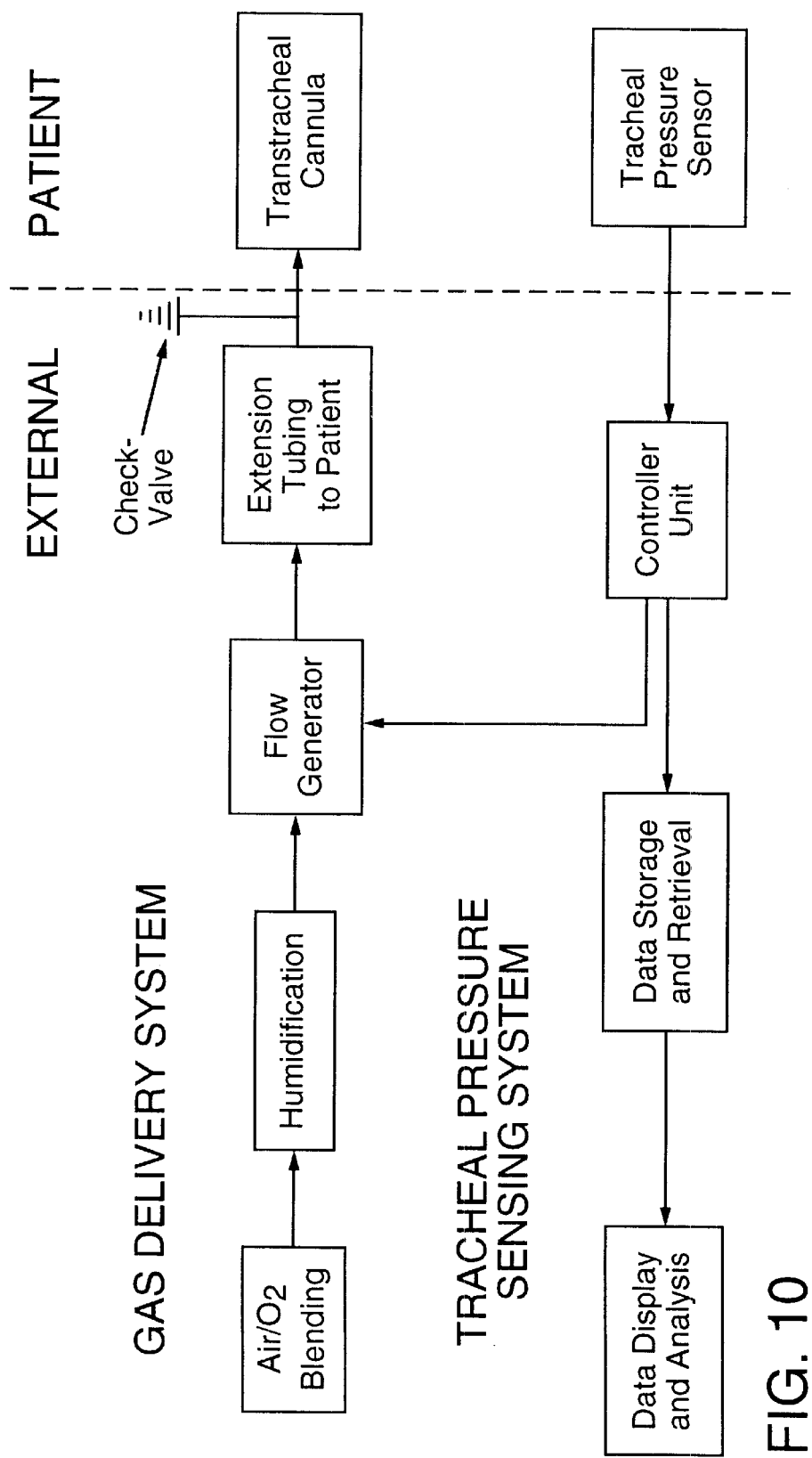
FIG. 10 is a schematic illustration of a gas delivery and tracheal pressure sensing system in accordance with an embodiment of the present invention.

Components of transtracheal treatment devices in accordance with preferred embodiments of the invention are schematically illustrated in FIGS. 9 and 10. For clarity, two main components of the treatment system are a gas delivery system and a sensing system.

The gas delivery system shown in FIG. 10 is adapted to deliver, e.g., from an air/O$_2$ source, breathing gas flow rates of from about 4 to about 60 L/min through an extension tube and a transtracheal cannula. The preferred flow device which connects to the transtracheal cannula provides a constant flow at a relatively high pressure head. This pressure head would be required to overcome the high resistance of the relatively small diameter transtracheal cannula, discussed below.

Figure 11:
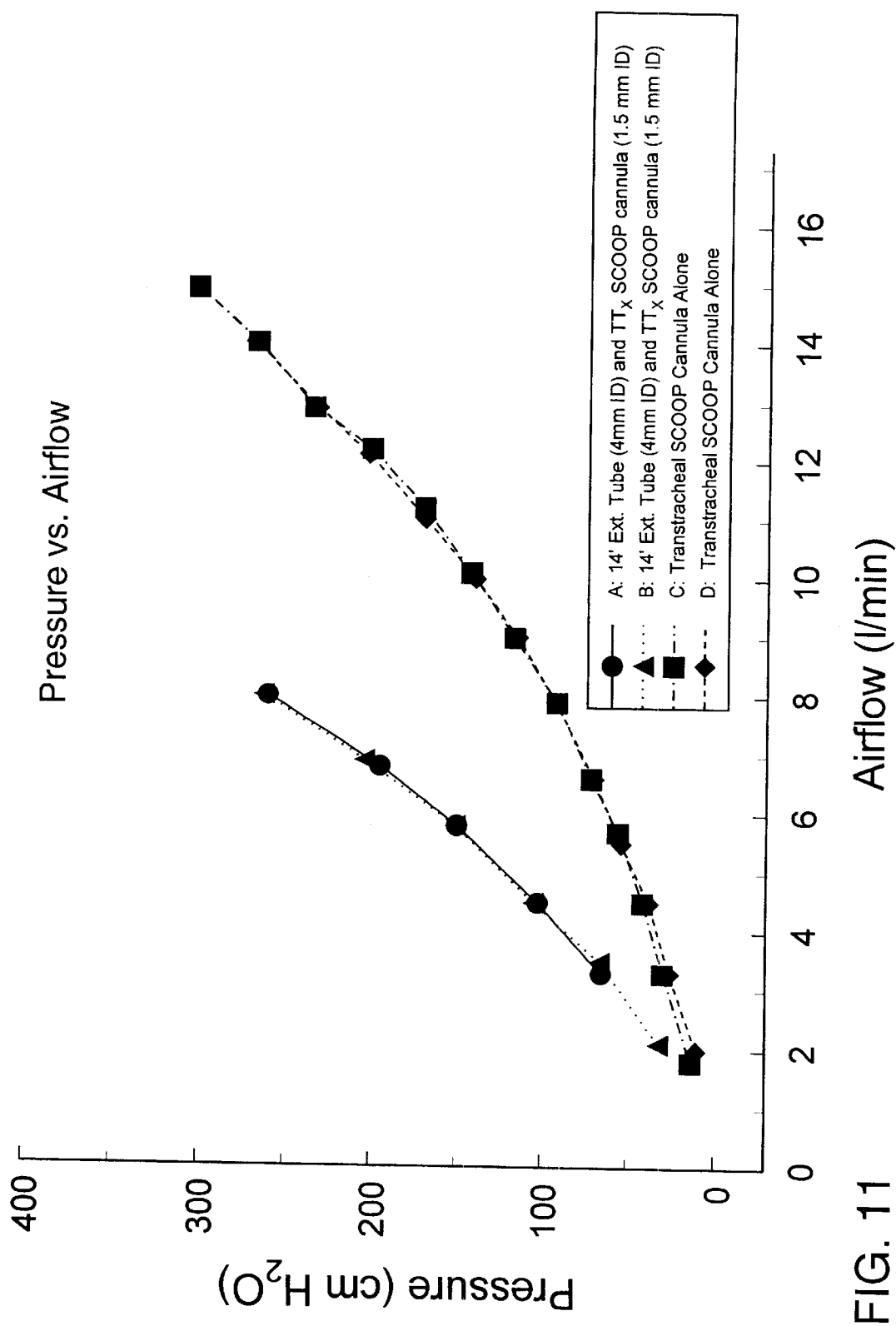
FIG. 11 shows pressure versus airflow for flow through a 20 cm long transtracheal cannula (1.5 mm ID) and through both the cannula and a 14 foot length of extension tubing (4 mm ID).

The pressure head required to drive airflow through, e.g., a 20 cm long transtracheal cannula (1.5 mm ID) and through both the cannula and a 14 foot length of extension tubing (4 mm ID) has been examined. The results appear in FIG. 11 for pressure versus airflow. In this figure, trials A and B represent the pressure-flow relationship when pressure is measured upstream to the 14 foot extension tubing and transtracheal cannula. Trials C and D represent this relationship when pressure is measured just upstream to the transtracheal cannula, neglecting the drop in pressure across the extension tubing. For home use at the bedside, it is expected that a 6 to 8 foot length of extension tubing is all that will be required.

Figure 12:
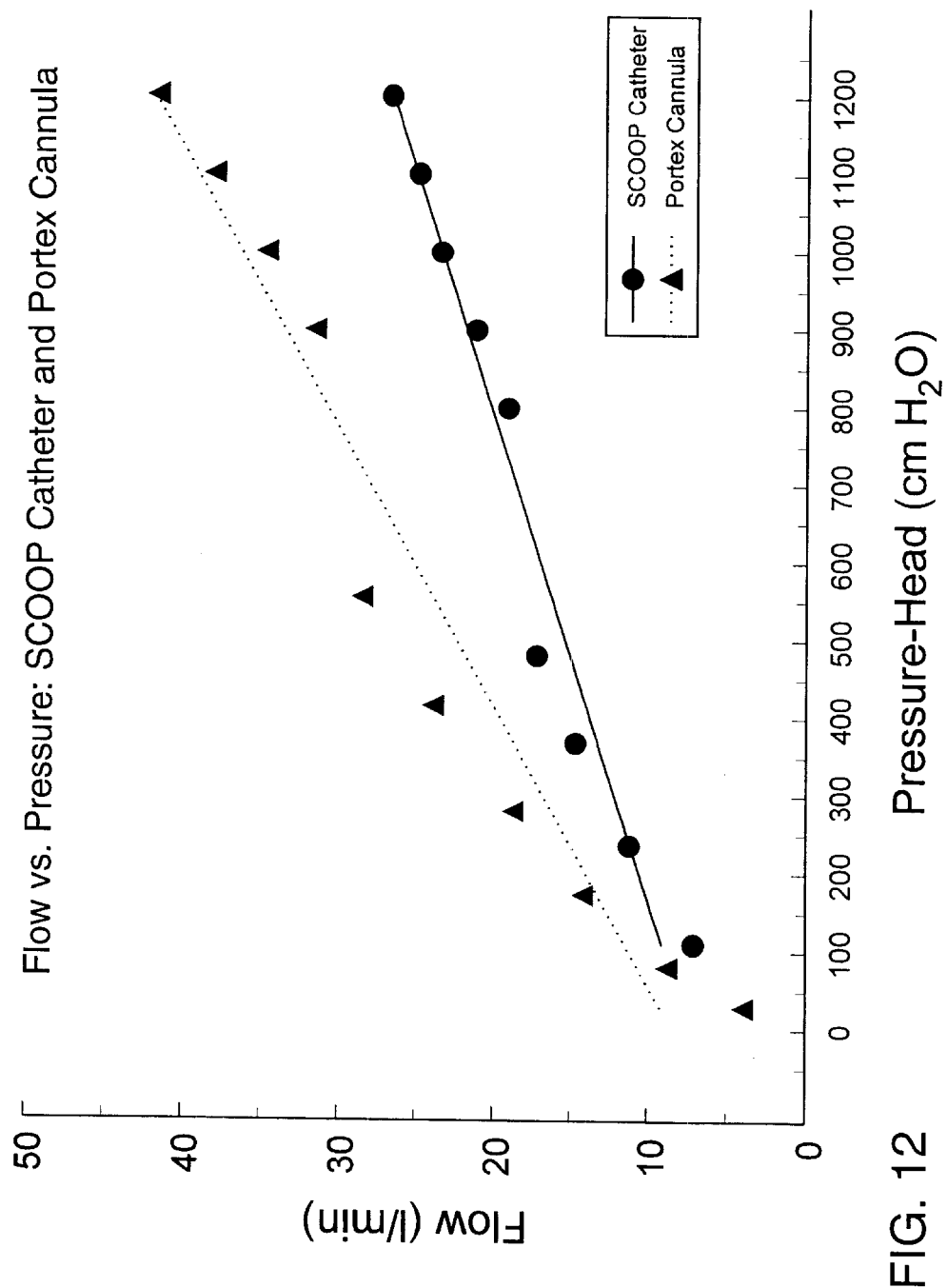
FIG. 12 shows airflow versus pressure the combination of a catheter and a six foot length extension tubing (4 mm ID).

Thus, pressure-flow relationships for the combination of a catheter and a six foot length of extension tubing system have also been examined. The results appear in FIG. 12 for airflow versus pressure. As previously noted, the extension tubing is 4mm internal diameter. A commercially available catheter sold under the designation SCOOP by Transtracheal Systems and a commercially available cannula sold under the designation PORTEX by Sims, Inc. were both evaluated. As can be seen, a pressure head of up to 1,200 cmH$_2$O may be required to achieve flow rates of 40–45 L/min through the PORTEX cannula. Such pressure heads only produce approximately 25 L/min through the SCOOP catheter. Therefore, a two-staged approach may be appropriate. For example, with patients who require relatively low flows of less that 25 L/min, a SCOOP-type catheter might suffice, whereas a larger PORTEX-type cannula may be selected to provided the higher flow rates. A larger bore extension tubing would also be helpful since it will allow for flow delivery through the transtracheal cannula at a lower pressure head. Therefore, an extension tubing of approximately 3 feet in length and 5–10 mm internal diameter may be particularly desirable.

Figure 13:
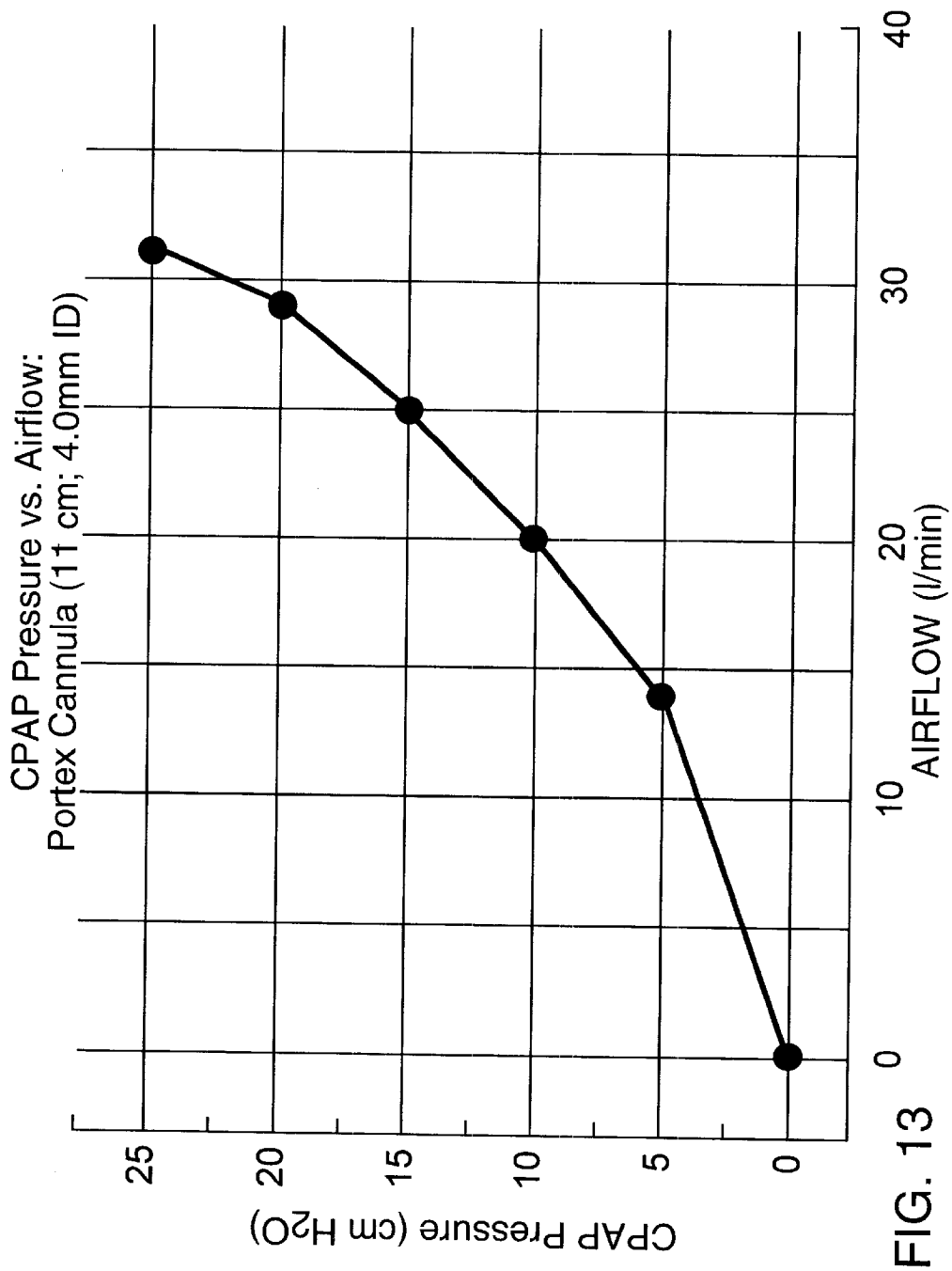
FIG. 13 shows pressure versus airflow for flow through a 11 cm long transtracheal cannula (4 mm ID).

The pressures required to generate flows of up to 40 L/min through a 4mm ID transtracheal tube of about 11 cm in length have also been measured and the results are shown in FIG. 13. These parameters define an exemplary minimum length and maximum diameter of the cannula to get the necessary air into the trachea. Thus the illustrated relationship describes the minimum pressure head required to drive such higher levels of airflow into the trachea.

Input to the gas flow controller unit of the flow generator includes the physician prescribed level of insufflation flow $\dot{V}_{IN}$. The unit needs to sense the flow rate and supply a head of pressure required to generate that flow. From the foregoing, the flow generator shown in FIG. 10 is preferably capable of providing, e.g., between 4 and 60 L/min through the extension tubing and transtracheal cannula and to that end should preferably be capable of generating pressure up to about 1,500 cmH$_2$O. Depending on the size of the transtracheal cannula, the working range will likely be between 100 and 400 cmH$_2$O.

In hypoxemic patients, it may be desirable to blend supplemental oxygen into the gas stream, and the gas supply system can be suitably adapted to provide for selective, controlled oxygen blending in to the air delivered to the patient. Suitable oxygen blending systems are commercially available, e.g., Bird Oxygen Blender, Ohmeda Blender, and Sensor Technologies, Teledyne, Inc. Also, for purposes of safety and patient comfort, it may be desirable to fully humidify the gas stream to minimize irritation of the airway mucosa.

The transtracheal catheter is schematically shown in FIG. 10. The transtracheal catheter is an elongated flexible tube formed of a bio-compatible material. In accordance with the invention, the proximal end of the catheter preferably has a suitable connector structure for connecting the tube to the air supply, generally by way of an extension tubing that extends from the gas flow generating system to the patient. The distal end of the tube preferably has a plurality of perforations to ensure the free flow of air and is adapted for disposition in the patient's respiratory passage. The tube can have an inside diameter, for example, of 1.0 mm (SCOOP) or 4.0 mm (PORTEX) for adult patients and about half that for pediatric patients.

The tube wall structure and thickness is such as to permit flexure of the tube during insertion into the trachea while resisting permanent deformation, kinking or collapse. The tube may be partly or wholly reinforced to facilitate resistance to undesired collapse and/or may have a relatively soft or compliant tip to avoid injury during insertion or in use. The tube may also be suitably coated or impregnated with a material to facilitate insertion and removal, to promote healing of the insertion site, to avoid infection and/or to maintain patency of the patient's airway and of the inner lumen of the catheter.

Various transtracheal catheters are known and one of suitable diameter and length can be selected for incorporation in the gas delivery system of the invention. Exemplary transtracheal catheters and methods for inserting the same are disclosed in U.S. Pat. Nos. 5,181,509 and 5,090,408. Nevertheless, some modifications to the conventional transtracheal cannula will advantageously facilitate its adaption to the treatment of sleep apnea in accordance with the invention. First, the cannula can have a slightly larger internal diameter to facilitate gas delivery with lower driving pressure heads, as exemplified by the data shown in FIG. 12. Second, the cannula should preferably emerge so as to sit relatively flush with the skin. This modification makes the cannula less obtrusive, particularly for people who wish to close their collar. Third, the cannula can be adapted to be removed when not used during the daytime. In that event, a transtracheal button component (not shown in detail) could be inserted to seal the transtracheal hole and prevent its closure. Various button sizes may be provided, depending on the depth of the subcutaneous tissues, and a soft umbrella flange may be utilized to prevent the button from popping out. Such a flange has been developed by Medtronic but is used for anchoring a pressure transducer in the breastbone. The Medtronic product, which is incorporated in their fully implantable hypoglossal nerve stimulating system, is a flexible silicone umbrella around the end of a cannula. The umbrella compresses when the cannula is inserted through tissue and opens when it reaches a cavity or lumen. When the cannula is removed, the umbrella inverts, and it is possible for the cannula to be removed. Other collapsible and/or selectively anchoring structures are known, e.g, in suprapubic catheters, and could be provided in accordance with the invention.

A pressure release mechanism may be provided as a fail-safe to prevent over-inflation of the lung. If provided, this pressure release mechanism should vent excess gas when pressure exceeds a selected threshold $P_{MAX}$. Accurate monitoring of the tracheal pressure, with feedback control to the gas flow generator, will minimize the tendency to over-inflation and its undesirable consequences.

As shown in FIG. 10, the tracheal pressure sensing system provided in accordance with a preferred embodiment of the invention has two principal components: a tracheal pressure sensor; and controller/logic circuits to control the gas delivery device. In addition to the $P_{TRACH}$ input from the sensor, the inputs to the controller may advantageously include the $P_{LIM}$ and other threshold and maximum values for the various parameters being monitored and input into the controller, to provide for feedback control and alarm modes as required. The output from the controller unit preferably includes a signal to either turn the flow generator on and off, to increase flow, or to divert the flow from the cannula system, as appropriate. A data storage and retrieval system may also be advantageously operatively coupled to the controller unit and/or tracheal pressure sensor to record and access waveforms from the $P_{TRACH}$ signal and from the $\dot{V}_{OUT}$ signal during patient testing. In addition, the data display and analysis units preferably display physiologic signals and initialize $\dot{V}_{IN}$ and $P_{LIM}$ settings, and will calculate physiologic parameters (time constant τ, $P_{CRIT}$, $R_S$, and $P_{TRACH}$ at $\dot{V}_{IN}$ level) to provide feedback/data to clinicians monitoring therapy.

The tracheal pressure sensor can advantageously be built into the transtracheal cannula. For example, a separate inner cannula can be provided with a port in the trachea. This cannula can then be connected to a standard strain gauge to transduce the pressure signal. Many manufacturers produce such gauges including Gould, Validyne, and Celesco. Alternatively, the pressure can be transduced in the trachea by incorporating a piezo sensor in the transtracheal portion of the cannula. Again, a number of manufacturers produce such sensors for medical/physiologic purposes including Milar, Camtech, Gaeltec and Synetics. In accordance with the present invention the sensor should be capable of sensing pressure fluctuations in the range of −100 to +100 $cmH_2O$, and optimally in the range of −50 to +50 $cmH_2O$.

The tracheal pressure signal is processed to provide data relevant to monitoring and controlling the efficacy of the gas delivery. Detection focuses on: (1) monitoring $P_{TRACH}$; and (2) terminating $\dot{V}_{IN}$ if $P_{TRACH}$ exceeds $P_{LIM}$, otherwise, continue $\dot{V}_{IN}$. Also, one or more of the following respiratory parameters may also be monitored: esophageal pressure, tidal volume and oximetry. Routine monitoring of sleep including electrocardiograms, electroencephalograms, and submental electromyogram may also be advantageous. Suitable monitors and processing systems for such monitoring and evaluation are known, generally.

EXAMPLES

Five tracheostomized patients with obstructive sleep apnea were studied. These patients were chosen because of their unique upper airway physiology that is characterized by the development of a positive $P_{CRIT}$ during sleep. In addition, the tracheostomy provided direct access to the trachea for pressure monitoring and transtracheal insulation (see below).

In these patients, the tracheostomy was occluded and a thin transtracheal (SCOOP, Transtracheal Systems, Inc., Denver, Colo.) cannula was inserted through a tracheostomy cap through which transtracheal insufflation was administered at flow rates up to 45 liters/minute. Tracheal pressure was monitored with a stub adaptor inserted into the tracheostomy cap. Pressure in the pleural space (esophagus) outside the lungs ($P_{ES}$) was monitored with a standard esophageal balloon catheter placed perinasally in the mid-esophagus. Airflow coming out the upper airways $\dot{V}_{OUT}$ was monitored with a tight fitting oronasal face mask. Standard polysomnography was also performed to distinguish sleep-wake state.

Patterns were developed on a test bed which included a tracheal pressure sensor, computer, solenoid valve and air compressor as illustrated in FIG. 9. The tracheal pressure $P_{TRACH}$ was monitored and digitized. $\dot{V}_{IN}$ was set between 0 and 45 liters/minute. Flow from the air compressor was applied either to the patient via a transtracheal cannula or vented directly to atmosphere by the solenoid valve. The solenoid was controlled by a computer, as detailed below.

Tracheal pressure was digitized and monitored continuously. A pressure limit $P_{LIM}$ was set, above which $P_{TRACH}$ would not be allowed to rise. When tracheal pressure remained below $P_{LIM}$, a constant level of airflow $\dot{V}_{IN}$ was delivered to the patient. When this $P_{LIM}$ was surpassed, the computer was programmed to divert air from the patient to atmosphere.

The following respiratory parameters were also monitored: esophageal pressure, tidal volume and oximetry. Routine monitoring of sleep included electrocardiograms, electroencephalograms, and submental electromyogram.

Two protocols were conducted. First, the respiratory responses were assessed during periods of time as the flow rate through the tracheal cannula was varied randomly at levels of 0, 5.0, 7.5, 10.0, 12.5, 15.0, 30 and 45 L/min. The level of flow that was associated with improved breathing patterns was then identified. This level was then applied continuously during sleep for 180 minutes to determine how effectively obstructive apneas were eliminated.

Exemplary results are illustrated in FIGS. 14–31.

Figure 14:
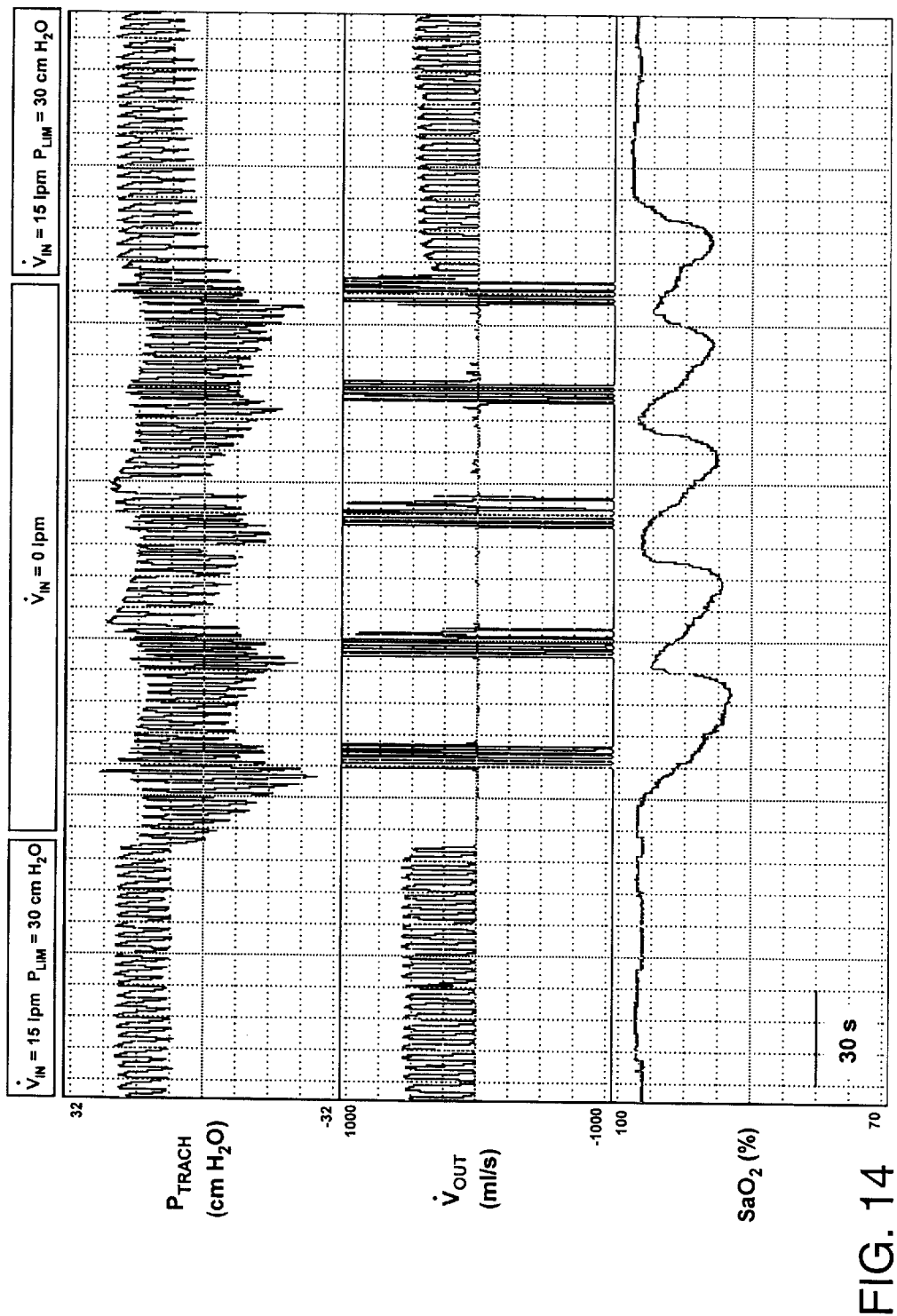
FIG. 14 is a trace of tracheal pressure ($P_{TRACH}$), airflow through the nose and mouth ($\dot{V}_{OUT}$) and oxyhemoglobin ($SaO_2$) over time for a typical patient with obstructive sleep apnea during non-REM sleep.

FIG. 14 illustrates the case where $\dot{V}_{IN}$ is zero, a baseline recording during sleep, bracketed by two periods of TTI ($\dot{V}_{IN}$=15 L/min., $P_{LIM}$=30 $cmH_2O$) before and after the baseline period. Typical obstructive apneas are characterized by periods of zero airflow out the upper airways $\dot{V}_{OUT}$, despite marked inspiratory deflections in $P_{TRACH}$ which augment with each succeeding breath until micro-arousals from sleep occur. Marked oxyhemoglobin desaturations occurred after each apneic episode (lower signal, dips in $SaO_2$). At that point, the airway opens, allowing for resumption of airflow ($\dot{V}_{OUT}$).

In contrast, TTI before (left side) and after (right side, FIG. 14) this control period abolished markedly negative $P_{TRACH}$ swings, desaturation and micro-arousals (not shown) during non-REM sleep. During TTI, a continuously fluctuating outward flow is recorded through the nose and mouth ($\dot{V}_{OUT}$).

Figure 15:
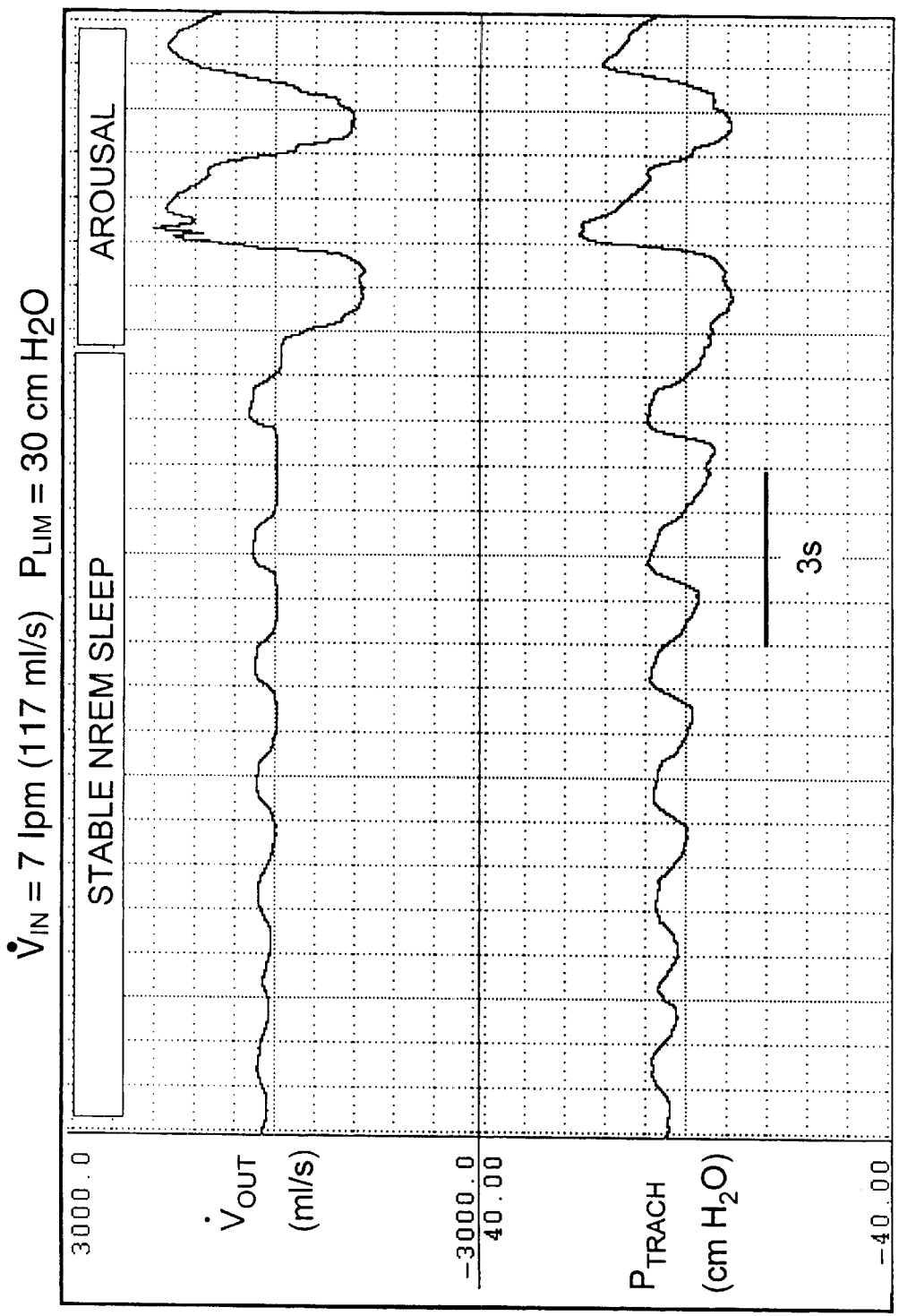
FIG. 15 is a trace of airflow through the nose and mouth ($\dot{V}_{OUT}$) and tracheal pressure ($P_{TRACH}$) over time when an exemplary obstructive sleep apnea patient is receiving 7 L/min insufflation flow ($\dot{V}_{IN}$) during sleep.

FIG. 15 shows an example of an inadequate level of $\dot{V}_{IN}$ in an apneic patient during non-REM sleep. Specifically, FIG. 15 illustrates tracheal pressure $P_{TRACH}$ and airflow through the nose and mouth $\dot{V}_{OUT}$ over time when the patient is receiving 7 L/min insufflation flow $\dot{V}_{IN}$ and $P_{LIM}$ is set at 30 $cmH_2O$. During inspiratory negative deflections in $P_{TRACH}$, $\dot{V}_{OUT}$ fell to zero, indicating that the upper airway occluded. During these inspirations, no air enters through the upper airways (air exits through the upper airways, $\dot{V}_{OUT}$ remains positive), indicating that $\dot{V}_{IN}$ remains the sole source of air to inflate the lungs. Progressively augmenting inspiratory swings in $P_{TRACH}$ are observed, indicating that this level of $\dot{V}_{IN}$ is not meeting the patient's ventilatory demand. Because $\dot{V}_{IN}$ is inadequate, the patient arouses from sleep (right side of FIG. 15) and oxygenation falls. During arousal, note that the patient now inspires through his upper airway ($\dot{V}_{OUT}$ becomes negative), indicating that the upper airway had reopened.

Figure 16:
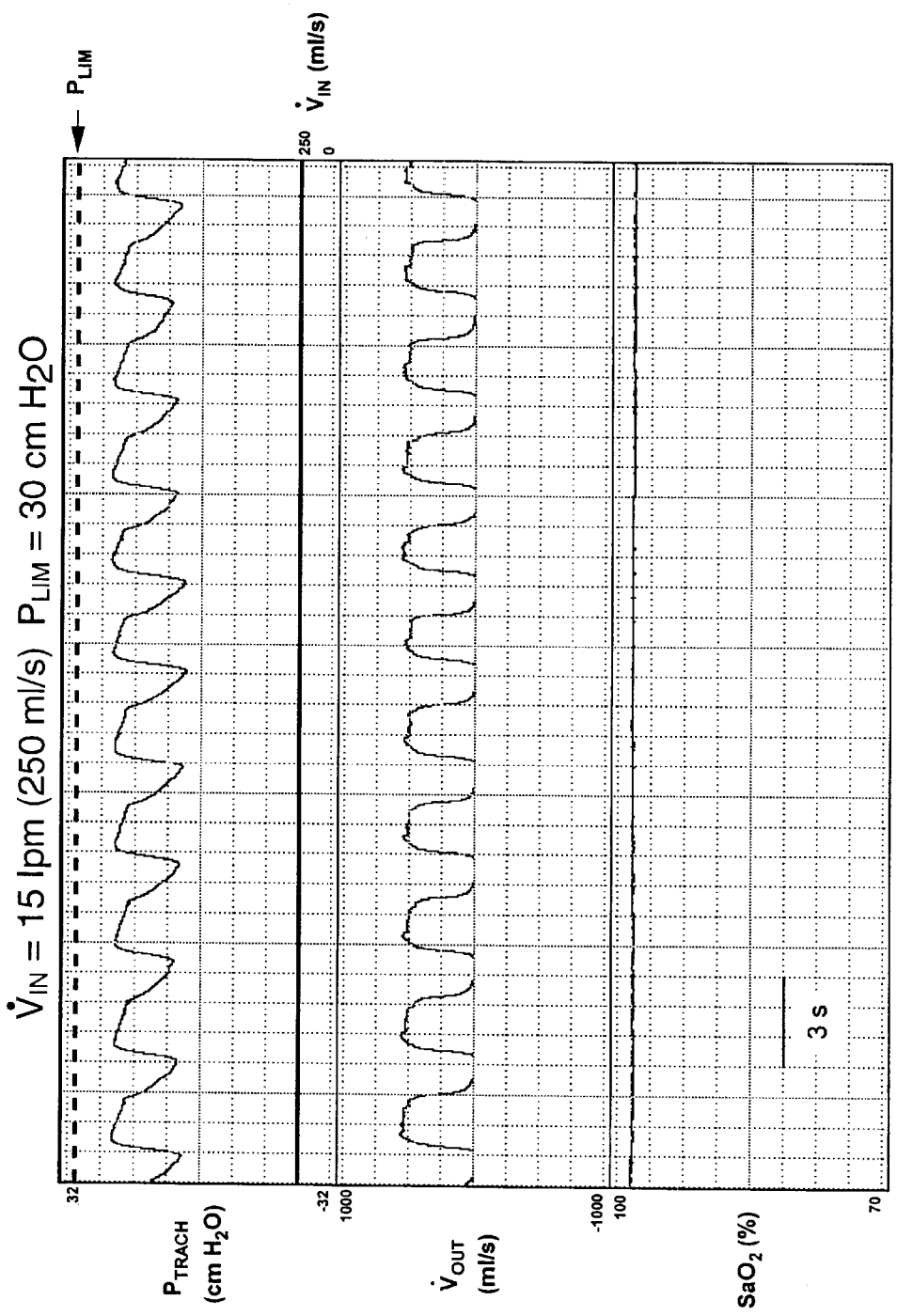
FIG. 16 is a trace of airflow through the nose and mouth ($\dot{V}_{OUT}$) and tracheal pressure ($P_{TRACH}$) over time during stable sleep when an exemplary obstructive sleep apnea patient is receiving 15 L/min insufflation flow ($\dot{V}_{IN}$) and the tracheal pressure limit ($P_{LIM}$) is set at 30 $cmH_2O$.

FIG. 16 illustrates the case where there is an adequate level of $\dot{V}_{IN}$ in accordance with one aspect of the invention. In this illustration, $P_{TRACH}$ and $\dot{V}_{OUT}$ are shown over time during stable stage II non-REM sleep when the patient is receiving 15 L/min $\dot{V}_{IN}$ and $P_{LIM}$ is set at 30 $cmH_2O$. At this level of $\dot{V}_{IN}$, a stable breathing pattern is observed without micro-arousal from sleep or oxyhemoglobin desaturations. $\dot{V}_{OUT}$ remains above zero throughout inspiration and expiration, indicating that the patient is breathing solely from the $\dot{V}_{IN}$ source. During inspiratory (downgoing) deflections in $P_{TRACH}$, $\dot{V}_{OUT}$ falls to zero, indicating that all inflow, $\dot{V}_{IN}$, is diverted to the lung rather than venting through the upper airways. Negative $P_{TRACH}$ swings are no longer augmentive, indicating that the patient's ventilatory demands are now being met. Because $\dot{V}_{IN}$ is now adequate, the patient no longer arouses from sleep and does not experience any decreases in oxygenation, thereby assisting in the elimination of apneas and hypopneas. Nevertheless, $P_{TRACH}$ swings are large (approximately 16 cmH$_2$O), indicating that TTI is not fully meeting this patient's flow requirement.

Figure 17:
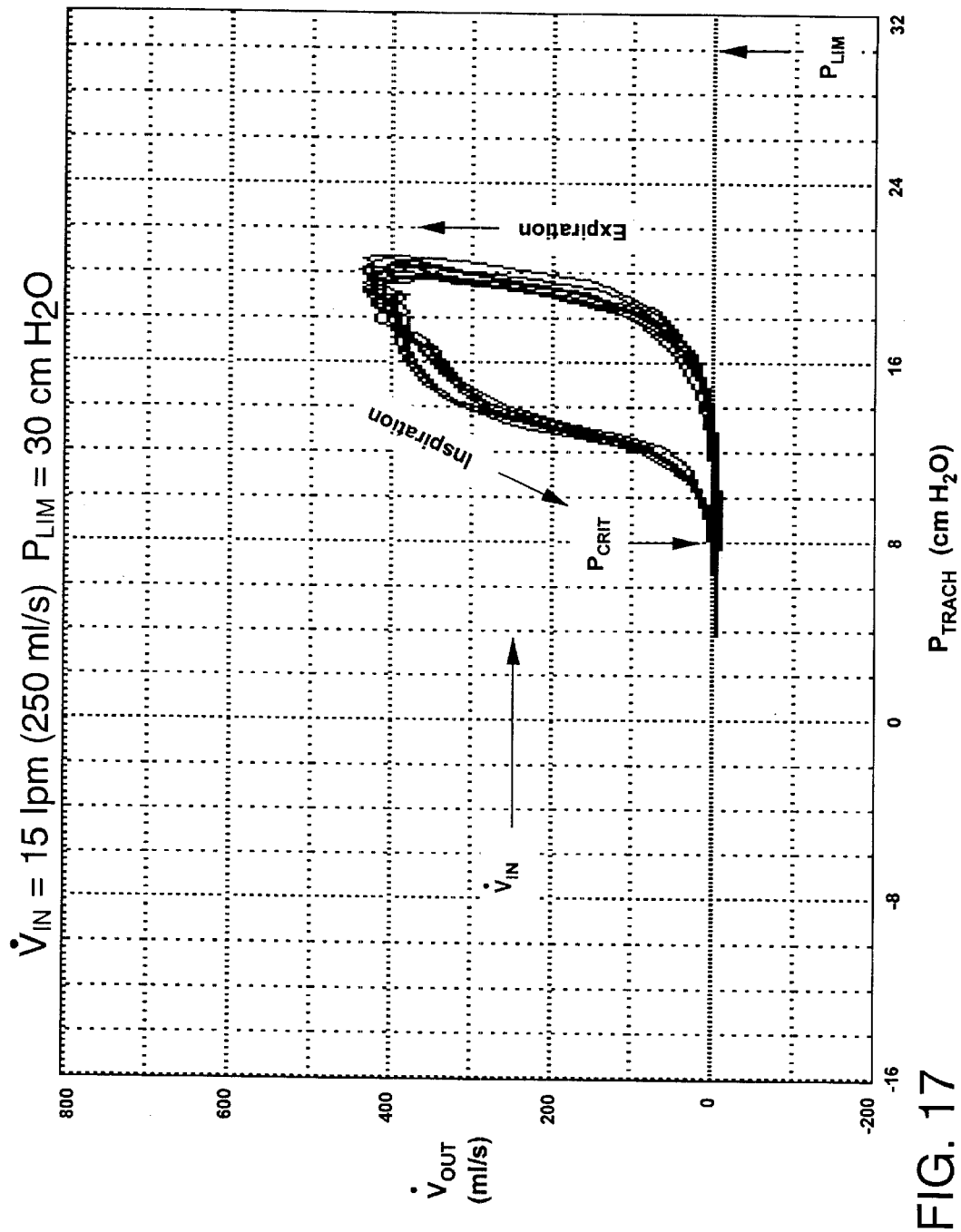
FIG. 17 is a graph of $\dot{V}_{OUT}$ versus $P_{TRACH}$ for a patient receiving 15 L/min. insufflation flow ($\dot{V}_{IN}$) at a $P_{LIM}$ of 30 $cmH_2O$ as illustrated in FIG. 16.

In FIG. 17, the corresponding graph of $\dot{V}_{OUT}$ versus $P_{TRACH}$ is observed for the breaths shown in FIG. 16. Each breath is described by a pressure-flow loop, each of which superimposes to delineate the pressure-flow relationship for the upper airway during inspiration (descending limb) and expiration (ascending limb). With each inspiration, $P_{TRACH}$ falls and flow venting out the upper airways ($\dot{V}_{OUT}$) falls to zero when $P_{TRACH}$ falls below $P_{CRIT}$ (see $P_{CRIT}$ labelled on graph). The expiratory limb shows an increase in $\dot{V}_{OUT}$ as $P_{TRACH}$ rises progressively above $P_{CRIT}$. The inspiratory and expiratory pressure-flow relationships are consistent with the conceptual framework illustrated in FIGS. 4–6 relating to the distribution of administered TTI flow, $\dot{V}_{IN}$, between the lungs and upper airways as the tracheal pressure changes throughout the respiratory cycle. Some clockwise hysteresis is observed between the inspiratory and expiratory limbs. In this example, a continuous flow of TTI is provided because $P_{TRACH}$ never rises to the level of $P_{LIM}$ as shown on the $P_{TRACH}$ axis.

Figure 18:
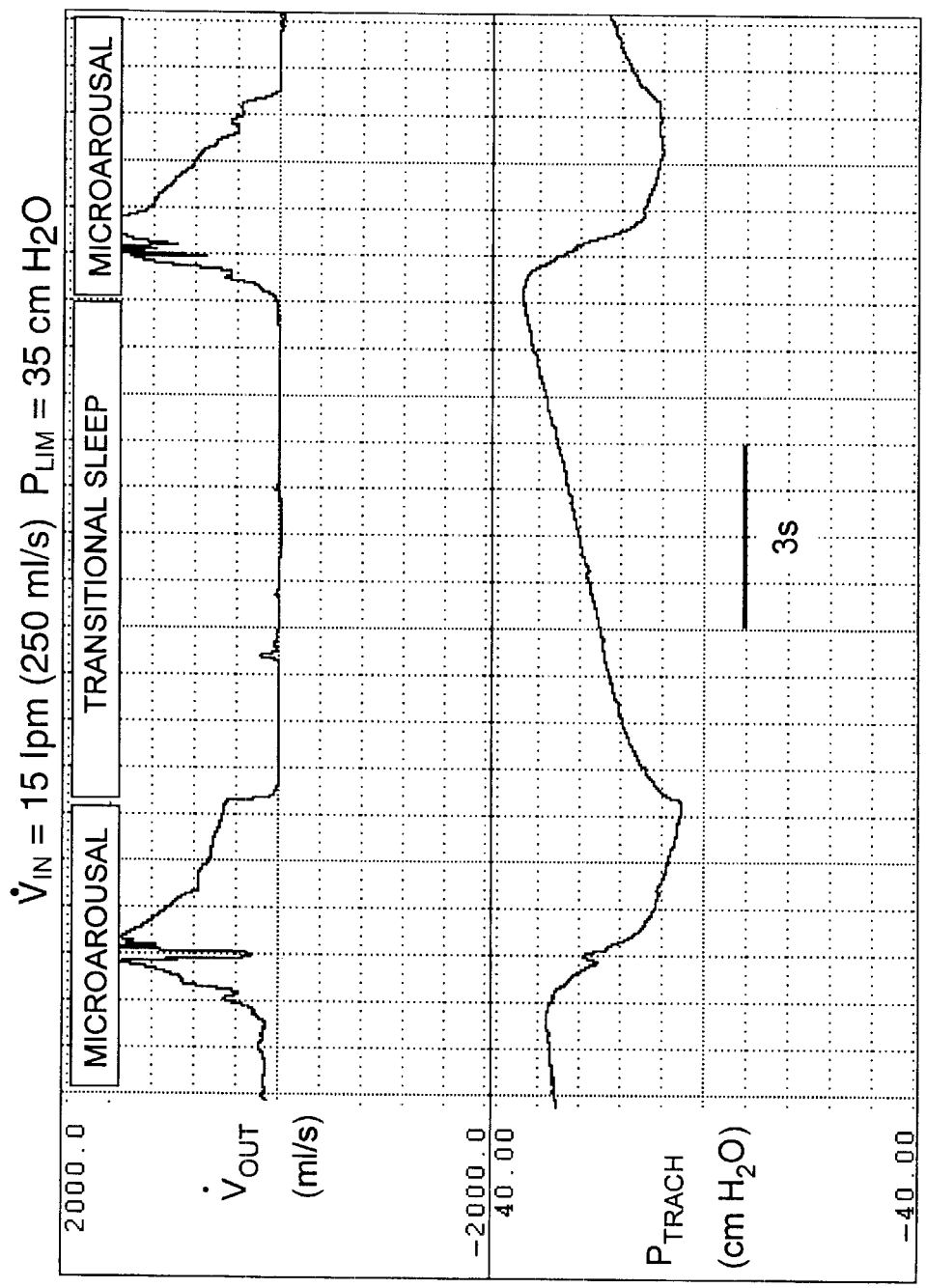
FIG. 18 is a trace of airflow through the nose and mouth ($\dot{V}_{OUT}$) and tracheal pressure ($P_{TRACH}$) over time when an exemplary obstructive sleep apnea patient is receiving 15 L/min insufflation flow ($\dot{V}_{IN}$) and the tracheal pressure limit ($P_{LIM}$) is set at 35 $cmH_2O$ during transitional sleep, demonstrating the occurrence of glottic apneas.

FIG. 18 illustrates $P_{TRACH}$ and $\dot{V}_{OUT}$ during transitional stage I non-REM sleep when $\dot{V}_{IN}$ equals 15 L/min. and $P_{LIM}$ is set at 35 cmH$_2$O for the same apneic patient illustrated in FIGS. 14, 16 and 17. In this example, $\dot{V}_{OUT}$ remains zero during a period of continuous TTI in transitional sleep (center), indicating the upper airways remain closed. $P_{TRACH}$ rises progressively during this period as $\dot{V}_{IN}$ continues to inflate the lungs. Downgoing tracheal pressure swings are absent, indicating that spontaneous inspiratory efforts are suppressed, presumably by lung inflation reflexes in this sleep stage. These episodes, not previously described in the medical literature, are referred to herein as "glottic" apneas, based on current findings in our laboratory indicating that the vocal cords close off the upper airways and respiratory efforts cease. Finally, these episodes are terminated by micro-arousals (see right and left sides of diagram), at which time $\dot{V}_{OUT}$ vents out the upper airways (the upper airways open) and $P_{TRACH}$ falls again. As the patient falls into transitional sleep, $P_{TRACH}$ rises again and another glottic apnea ensues.

We have determined the frequency of these glottic apneas during periods of TTI (utilizing $\dot{V}_{IN}$=15 L/min., $P_{LIM}$=30 cmH$_2$O) for three consecutive hours of sleep in five patients with obstructive sleep apnea. When comparing the apnea-hypopnea index (number of apneas and hypopneas/hour non-REM sleep, a measure of the severity of sleep apnea), we found no significant reduction in apnea-hypopnea index with TTI (44.6±31.7 episodes/hour, mean±SD) compared to without TTI (63.7±21.8 episodes/hour). Although TTI was associated with a reduction in obstructive breathing episodes from 63.8±21.8 to 15.7±20.2 episodes/hour, the frequency of glottic apneas increased from zero to 28.6±12.6 episodes/hour with TTI, thereby accounting for the lack of overall improvement in apnea-hypopnea index with these TTI settings.

It is clear that while continuous TTI holds some promise for alleviating obstructive sleep apnea for periods of stable sleep, marked sleep disordered breathing can characterize breathing with continuous TTI during transitional sleep. The glottic apneas continue to disrupt sleep, perpetuating the daytime hypersomnolence that afflicts patients with obstructive sleep apnea. Moreover, these glottic apneas are associated with large elevations in tracheal pressure. Such increases hyperinflate the lungs, and pose a substantial risk of pneumothorax and barotrauma.

In accordance with the present invention, barotrauma resulting from the development of high tracheal pressures greater than about 30 cmH$_2$O may be prevented, and sleep fragmentation resulting from recurrent glottic apneas may be eliminated. Both can be addressed by lowering $P_{LIM}$ to a prescribed level.

Of the patients tested, it was found that obstructive apneas are substantially reduced with a $\dot{V}_{IN}$ of 15 liters/min. Some patients may be treated with lower flow rates of about 8 to 10 L/min, and even as low as 4 L/min., where relatively low levels of ventilatory support are required. On the other hand, large inspiratory tracheal pressure swings and mid-inspiratory cessation of $\dot{V}_{OUT}$ suggest that higher flow rates are warranted in many apneic patients. Indeed, people normally generate peak inspiratory flow rates of 35–40 L/min while breathing at rest. Accordingly, ventilatory demand may be met with higher $\dot{V}_{IN}$ flow rates.

Figure 19:
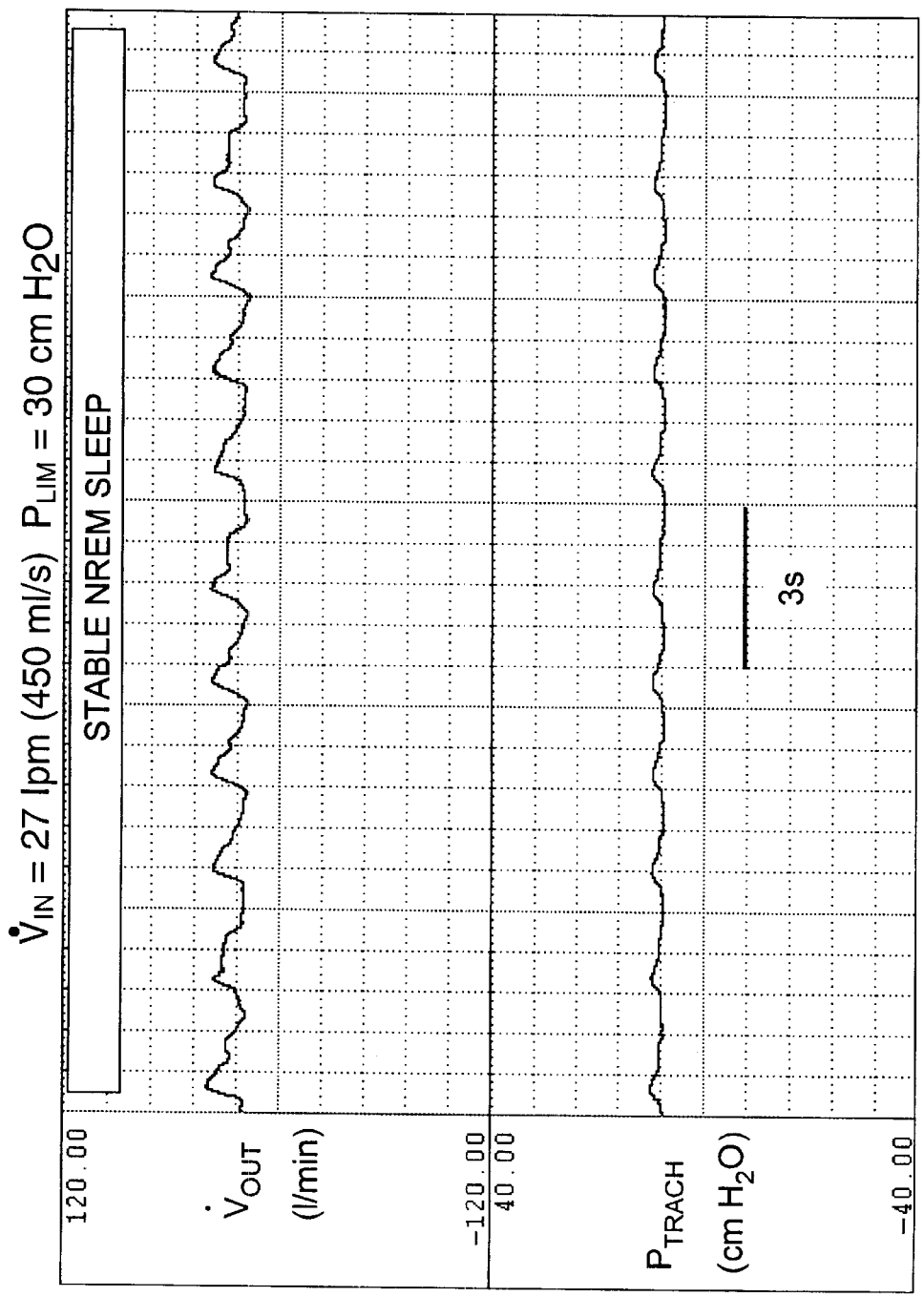
FIG. 19 is a trace of airflow through the nose and mouth ($\dot{V}_{OUT}$) and tracheal pressure ($P_{TRACH}$) over time when an exemplary obstructive sleep apnea patient is receiving 27 L/min insufflation flow ($\dot{V}_{IN}$) and the tracheal pressure limit ($P_{LIM}$) is set at 30 $cmH_2O$ during sleep.
Figure 20:
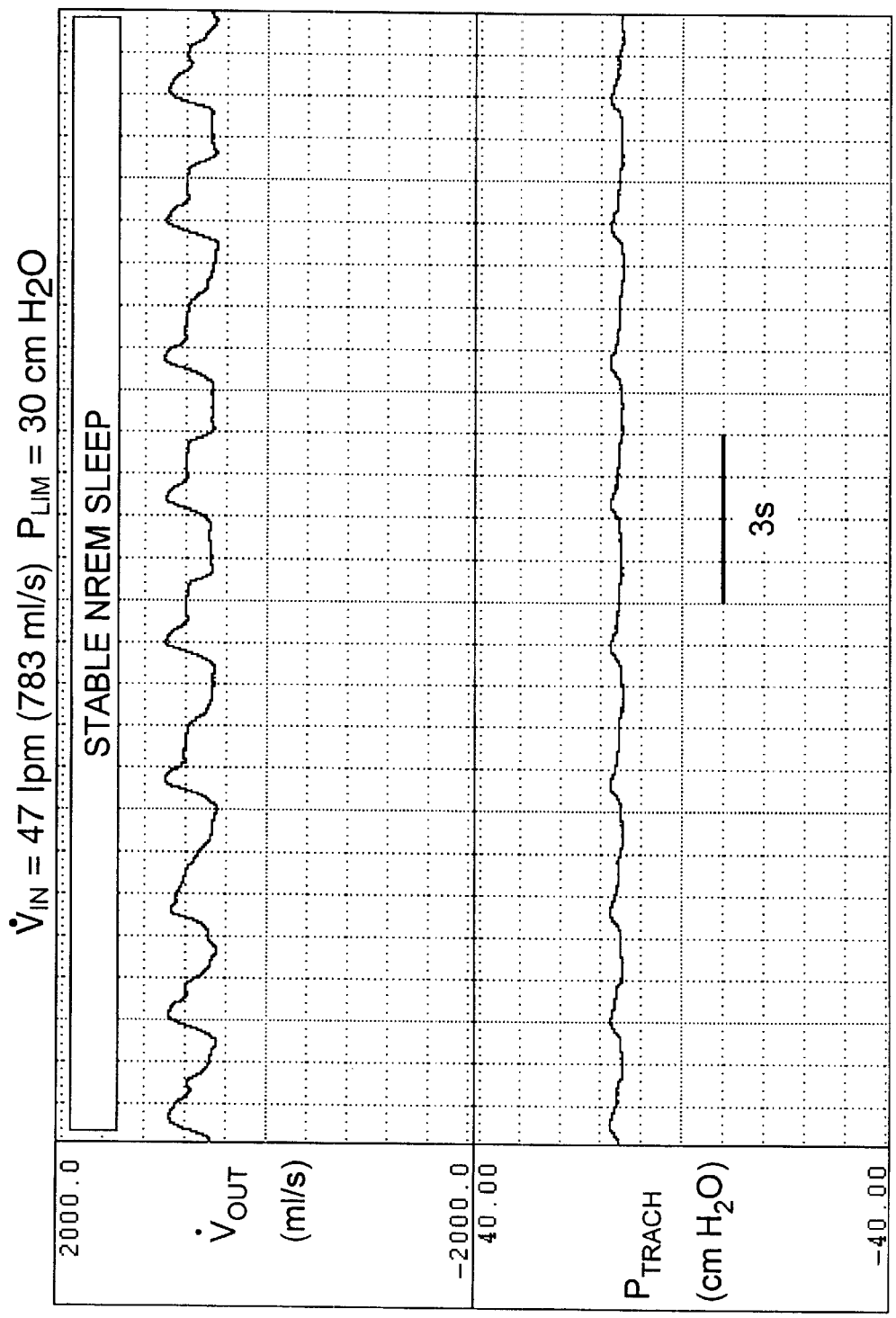
FIG. 20 is a trace of airflow through the nose and mouth ($\dot{V}_{OUT}$) and tracheal pressure ($P_{TRACH}$) over time when an exemplary obstructive sleep apnea patient is receiving 47 L/min insufflation flow ($\dot{V}_{IN}$) and the tracheal pressure limit ($P_{LIM}$) is set at 30 $cmH_2O$ during sleep.

The effect of such increases in $\dot{V}_{IN}$ on $P_{TRACH}$ and $\dot{V}_{OUT}$ signals are illustrated in FIG. 19 (27 L/min.) and FIG. 20 (47 L/min.) for periods of stable non-REM sleep. As can be seen, administration of higher flows $\dot{V}_{IN}$ produces $\dot{V}_{OUT}$ levels that never fall close to zero, indicating that air vents continuously out the upper airways. In fact, inspiration, signified by downward deflections in both signals, results in some reduction in the flow coming out the nose and mouth. Nevertheless, plenty of flow still exists during inspiration compared to that seen when $\dot{V}_{IN}$ is lower (FIG. 16). As a result, it is now possible for the patient to divert flow from the $\dot{V}_{IN}$ airstream into the lungs during inspiration without lowering tracheal pressure significantly. Conversely, the upper airways serve to vent excess air from the TTI source, with greater $CO_2O$ washout provided by TTI flow during expiration. This is in contrast with the greater deflections in tracheal pressure seen in FIG. 16 when $\dot{V}_{IN}$ is lower. From these data, it can be concluded that the tracheal pressure waveform can be utilized to determine whether $\dot{V}_{IN}$ is sufficient to meet the patient's ventilatory requirements. Typically, $\dot{V}_{IN}$ between 15 and 60 L/min may be preferred for many patients who require relatively high levels of ventilatory support. For example, higher flow rates of up to 40 or 50 L/min may be required to optimize the therapy in some patients with high ventilatory requirements, while many patients may be well treated with levels of 12.5 to 25 L/min. or lower. The utilization of such relatively high flow rates necessitates monitoring of tracheal pressure to prevent the development of glottic apneas and consequent buildup of excessively high levels of $P_{TRACH}$ during transitional sleep, when the glottic apneas occur.

Figure 21:
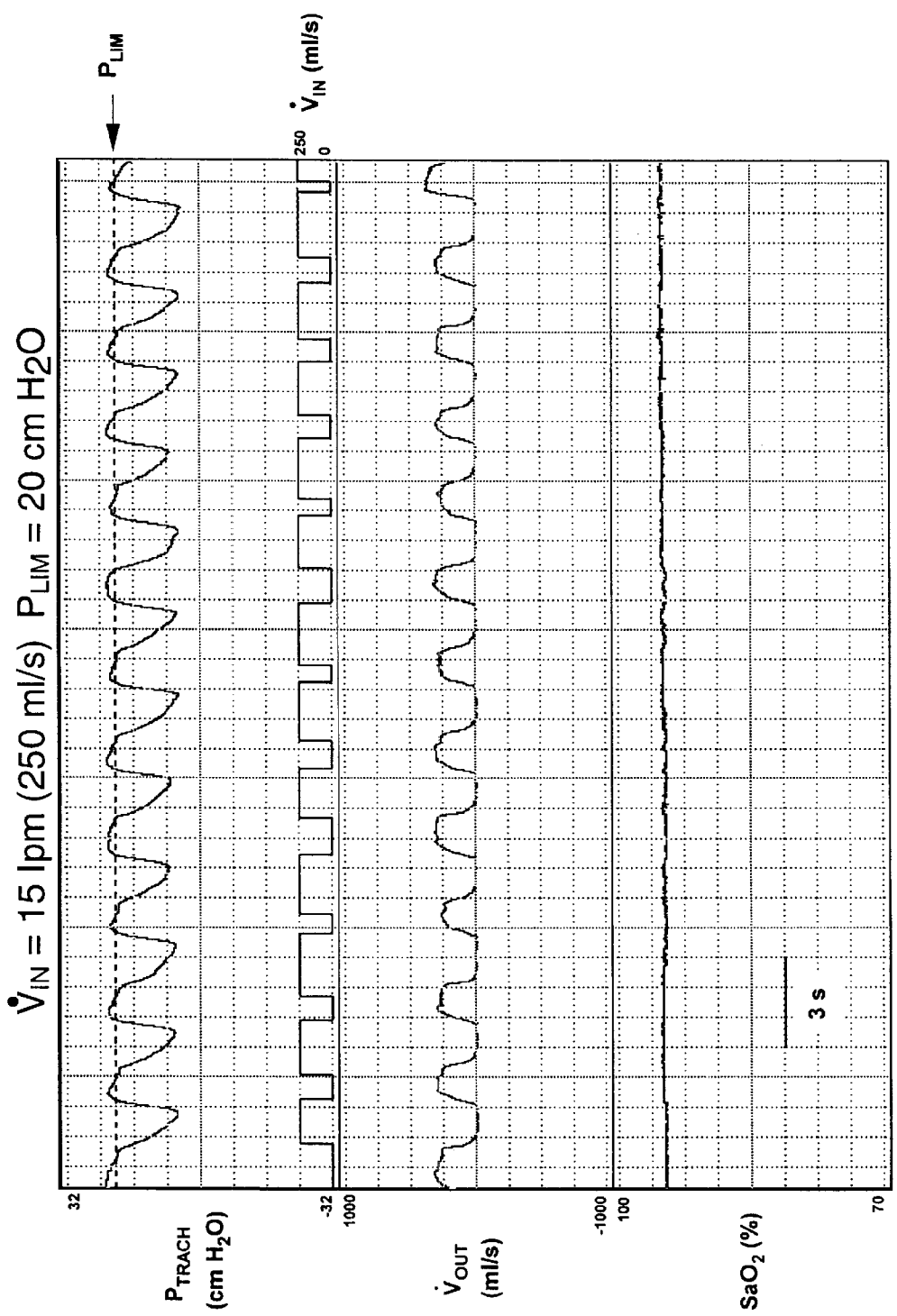
FIG. 21 is a graph of $P_{TRACH}$, $\dot{V}_{OUT}$, $SaO_2$ and $\dot{V}_{IN}$ versus time when an exemplary patient with obstructive sleep apnea is receiving a $\dot{V}_{IN}$ of 15 L/min. and a $P_{LIM}$ of 20 $cmH_2O$ during sleep.
Figure 22:
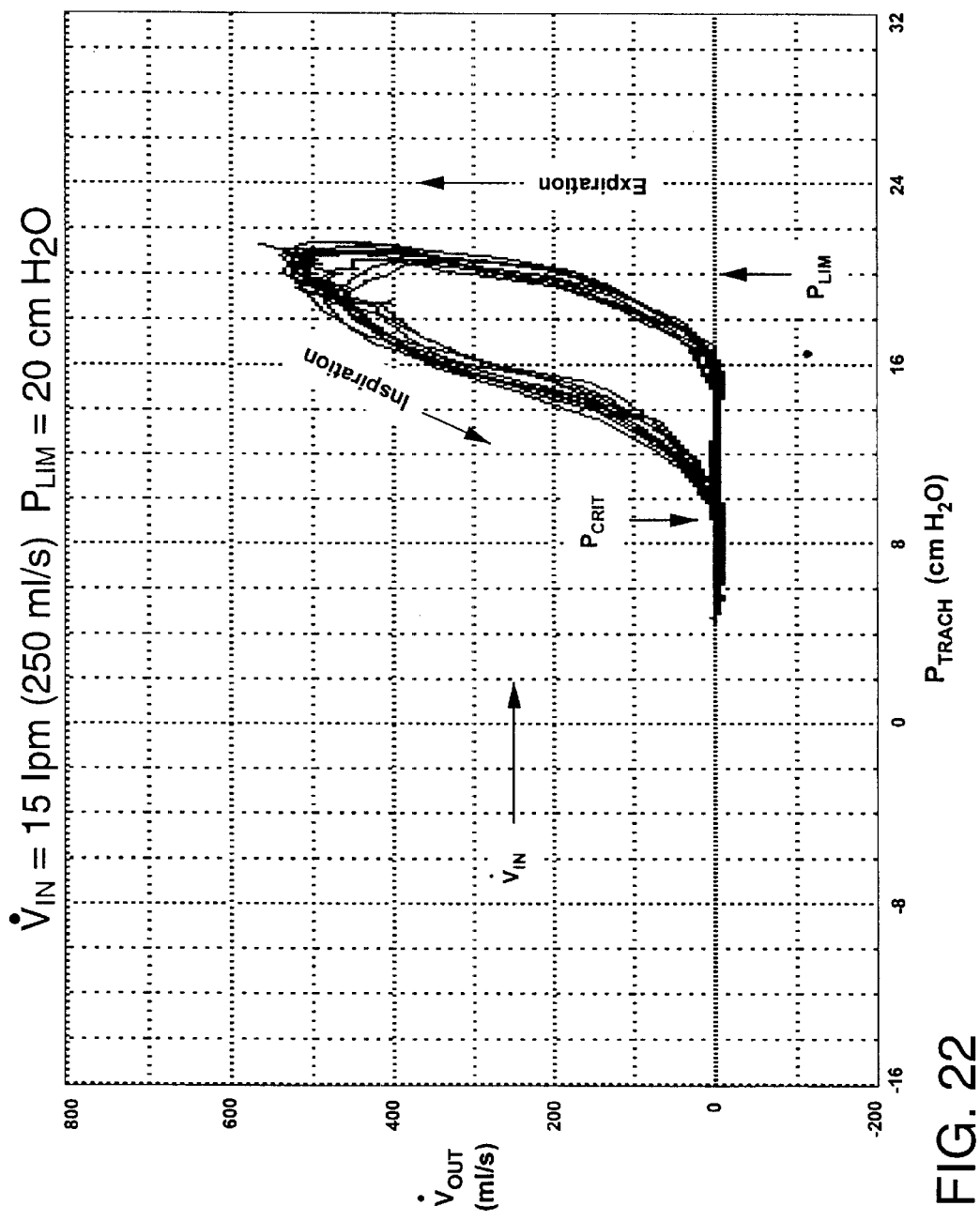
FIG. 22 is a graph of $\dot{V}_{OUT}$ versus $P_{TRACH}$ for a patient receiving 15 L/min. $\dot{V}_{In}$ and 20 $cmH_2O$ $P_{LIM}$ as illustrated in FIG. 21.

Accordingly, glottic apneas can be averted by preventing the buildup of tracheal pressure once the TTI gas is applied. This is accomplished by lowering $P_{LIM}$ substantially. In the examples that follow, the effect of lowering $P_{LIM}$ and raising $\dot{V}_{IN}$ is illustrated for the same patient shown in FIGS. 14 and 16–18. When $P_{LIM}$ was 20 cmH$_2$O and $\dot{V}_{IN}$ was 15 L/min., an intermittent ATTI pattern ensued (FIG. 21). $\dot{V}_{IN}$ was applied throughout inspiration (when downgoing swings in $P_{TRACH}$ were observed). Nevertheless, $P_{TRACH}$ swings remained quite elevated at approximately 16 cmH$_2$O, suggesting that ventilatory demand was not fully met. The corresponding pressure-flow relationship for the recording in FIG. 21 is shown in FIG. 22. In this graph, closure of the upper airways ($\dot{V}_{OUT}$ of zero) is associated with reductions in $P_{TRACH}$ below $P_{CRIT}$, as previously noted.

Figure 23:
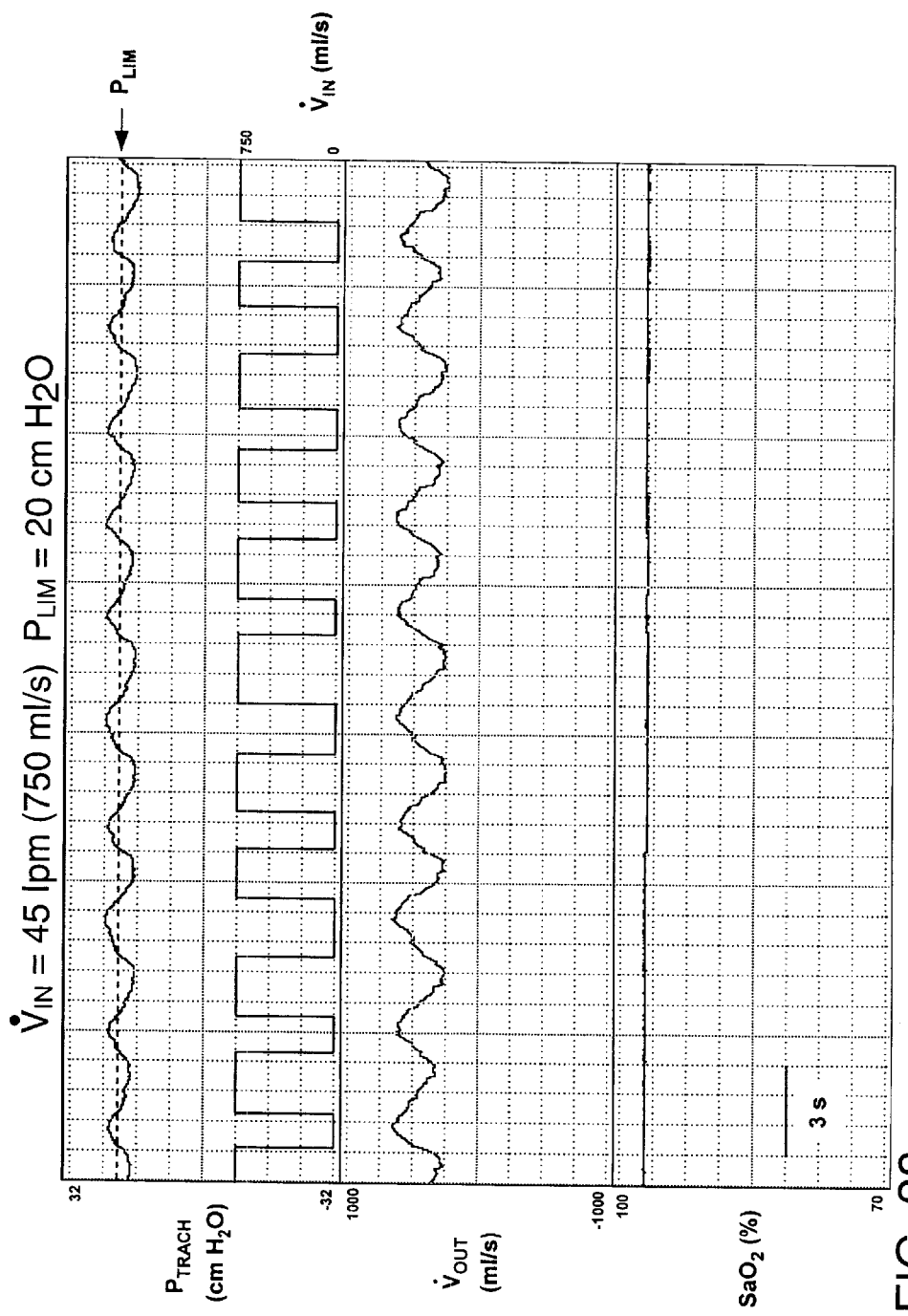
FIG. 23 is a graph of $P_{TRACH}$, $\dot{V}_{OUT}$, $SaO_2$ and $\dot{V}_{IN}$ versus time when an exemplary patient with obstructive sleep apnea is receiving a $\dot{V}_{IN}$ of 45 L/min. and a $P_{LIM}$ of 20 $cmH_2O$ during sleep.
Figure 24:
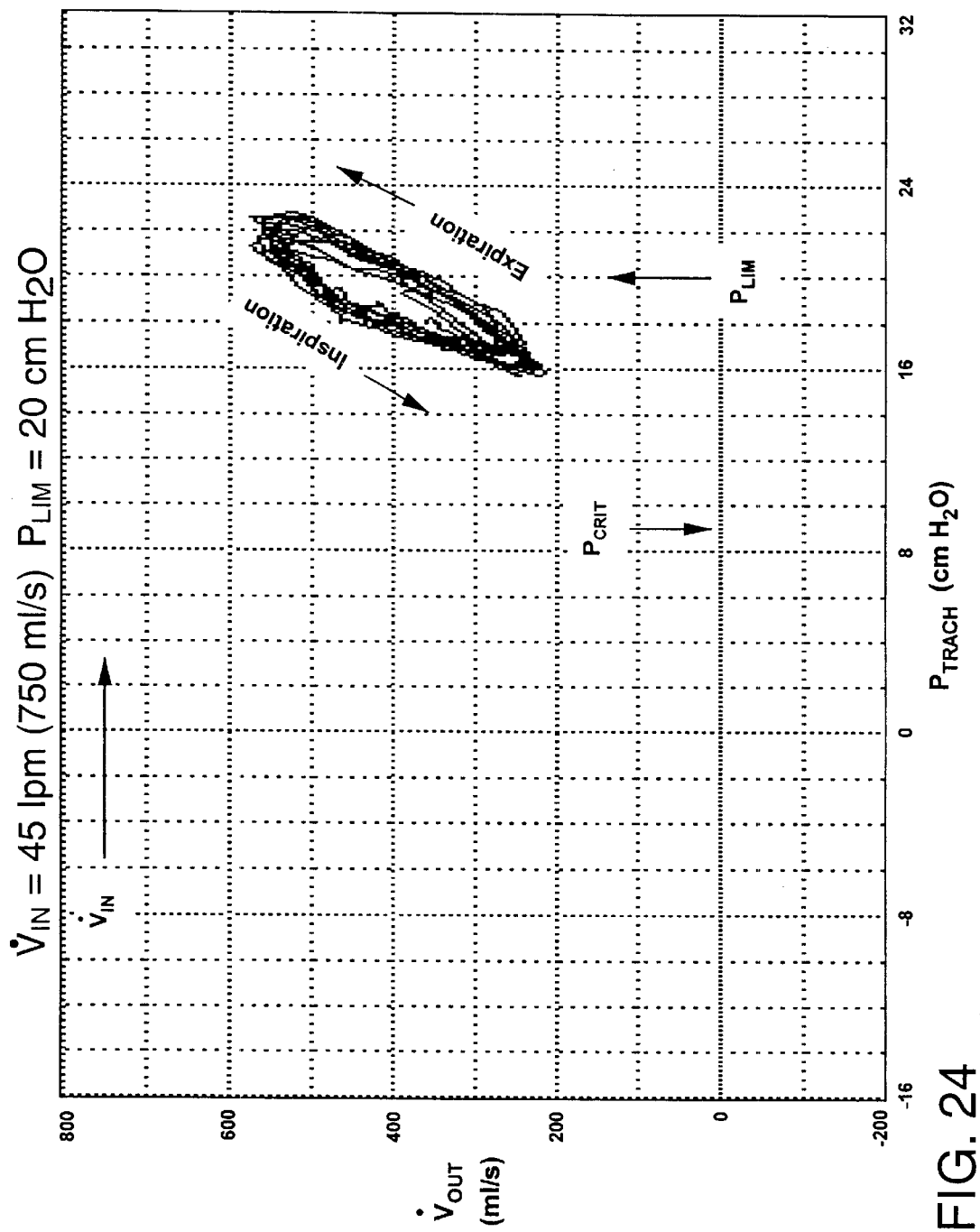
FIG. 24 is a graph of $\dot{V}_{OUT}$ versus $P_{TRACH}$ for a $\dot{V}_{IN}$ of 45 L/min. and $P_{LIM}$ of 20 $cmH_2O$ as illustrated in FIG. 23.

In FIG. 23, the negative swings in $P_{TRACH}$ are attenuated markedly by increasing $\dot{V}_{IN}$ to 45 L/min. ($P_{LIM}$=20 cmH$_2$O). The corresponding pressure-flow relationship for this recording appears in FIG. 24 which shows marked narrowing of the swings in $P_{TRACH}$ and $\dot{V}_{OUT}$ which remains positive throughout the respiratory cycle. In addition, hysteresis between the inspiratory and expiratory loops is reduced dramatically, now that upper airway closure and reopening is no longer occurring. This pattern best reflects a normal breathing pattern with an unobstructed upper airway, but is associated with significant CO$_2$ washout caused by expiratory levels of $\dot{V}_{OUT}$ of nearly 600 ml/s.

Figure 25:
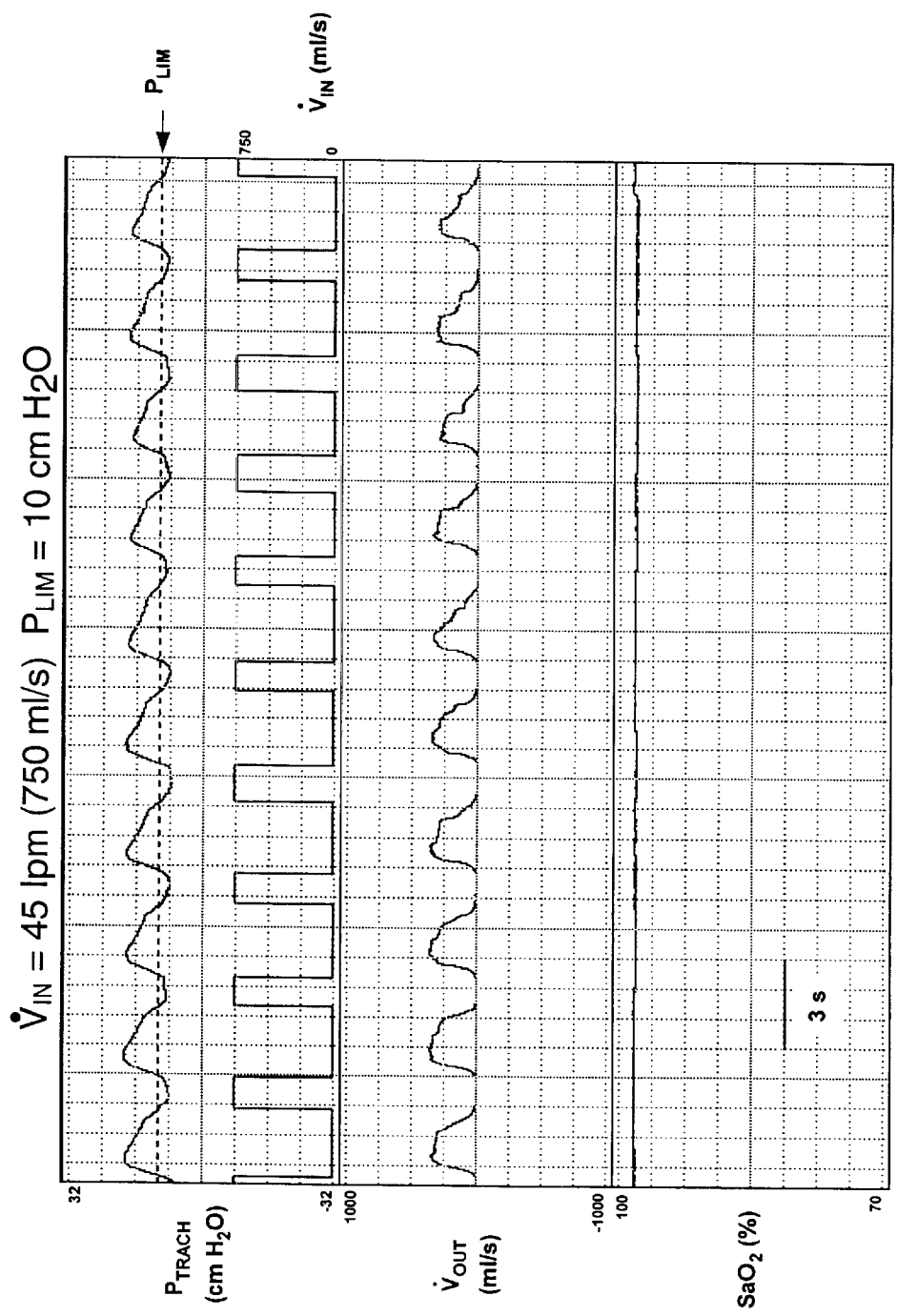
FIG. 25 is a graph of $P_{TRACH}$, $\dot{V}_{OUT}$, $SaO_2$ and $\dot{V}_{IN}$ versus time when an exemplary patient with obstructive sleep apnea is receiving a $\dot{V}_{IN}$ of 45 L/min. and a $P_{LIM}$ of 10 $cmH_2O$ during sleep.
Figure 26:
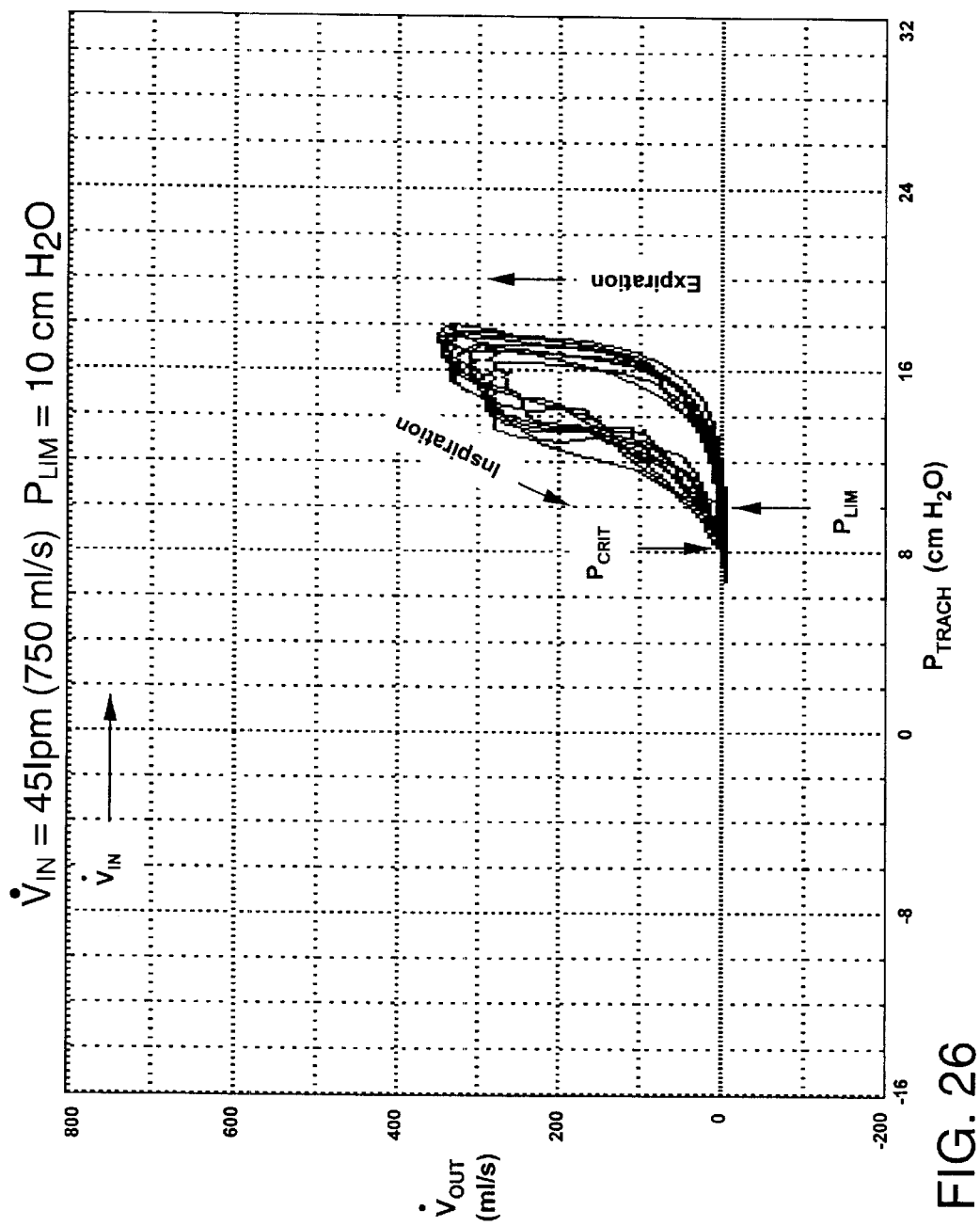
FIG. 26 is a graph of $\dot{V}_{OUT}$ versus $P_{TRACH}$ for a $\dot{V}_{IN}$ of 45 L/min. and a $P_{LIM}$ of 10 $cmH_2O$ as illustrated in FIG. 25.
Figure 27:
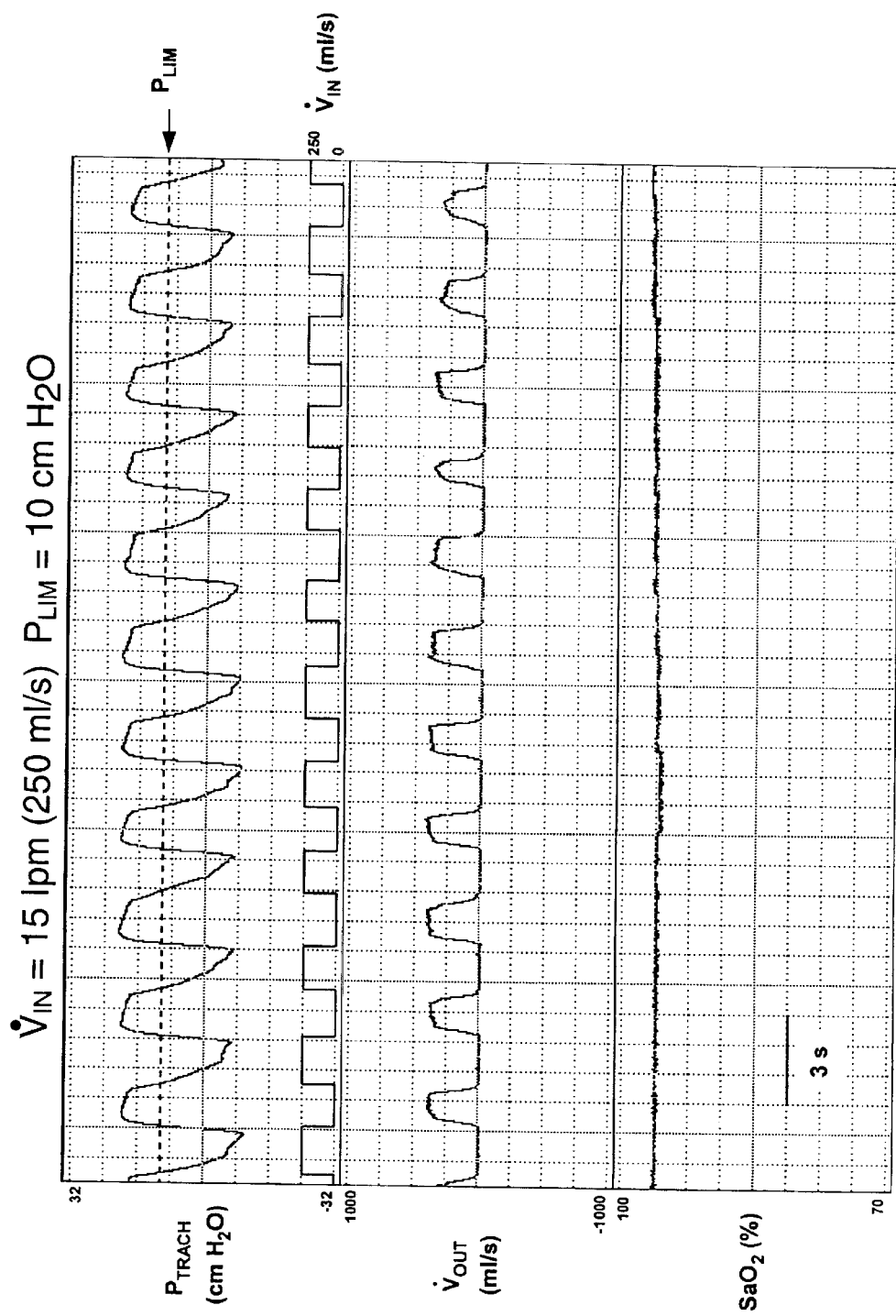
FIG. 27 is a graph of $P_{TRACH}$, $\dot{V}_{OUT}$, $SaO_2$ and $\dot{V}_{IN}$ versus time when an exemplary patient with obstructive sleep apnea is receiving a $\dot{V}_{IN}$ of 15 L/min. and a $P_{LIM}$ of 10 $cmH_2O$ during sleep.
Figure 28:
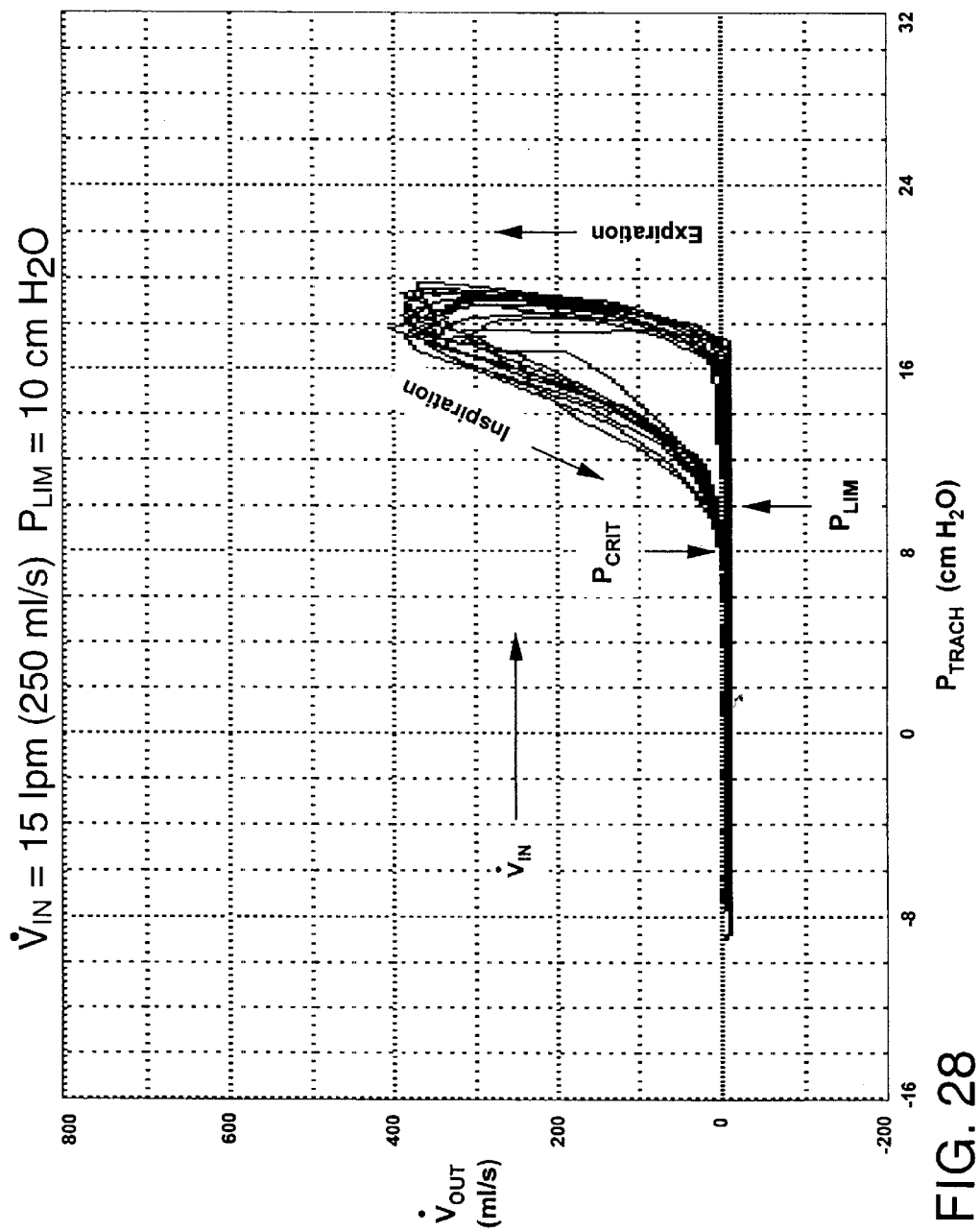
FIG. 28 is a graph of $\dot{V}_{OUT}$ versus $P_{TRACH}$ for a $\dot{V}_{IN}$ of 15 L/min. and a $P_{LIM}$ of 10 $cmH_2O$ as illustrated in FIG. 27.

To avoid excess leakage of flow and decrease CO$_2$ washout through the upper airways, we decreased $P_{LIM}$ to 10 cmH$_2$O ($\dot{V}_{IN}$ remained at 45 L/min.). The sleep recordings of respiratory signals and their corresponding pressure-flow graphs are illustrated in FIGS. 25 and 26, respectively. With a lower $P_{LIM}$, $\dot{V}_{IN}$ is now only applied in mid-inspiration, thereby decreasing expiratory levels of $\dot{V}_{OUT}$ and associated CO$_2$ washout. Nevertheless, inspiratory $P_{TRACH}$ swings remain only approximately 5–6 cmH$_2$O, indicating that the patient's ventilatory needs are largely met. Although $P_{TRACH}$ falls to the point of airway closure ($\dot{V}_{OUT}$ becomes zero), this phenomenon is only transient and not associated with much further decrease in tracheal pressure during inspiration.

Thus, the breathing patterns observed in FIGS. 21–26 illustrate how levels of inspiratory support can be varied by adjusting $\dot{V}_{IN}$ between 15 and 45 L/min. while expiratory leakage and CO$_2$ washout through the upper airways can be altered by varying $P_{LIM}$. In each case, the prescribed $\dot{V}_{IN}$ and $P_{LIM}$ were sufficient to avert the development of recurrent glottic apneas with their attendant morbidity from excessively high buildup of tracheal pressure and sleep fragmentation. The prevention in glottic apneas can be attributed to reflex responses that help maintain a stable spontaneous breathing pattern when TTI is applied intermittently rather than continuously, and when tracheal pressure is capped by $P_{LIM}$. These findings suggest that appropriate levels of $\dot{V}_{IN}$ and $P_{LIM}$ will maintain a suitable level of tracheal pressure to vent exhaled air freely through the upper airway, yet direct the TTI flow toward the lungs when the patient inhales.

In contrast to the findings in FIGS. 25 and 26 at a $\dot{V}_{IN}$ of 45 L/min. and $P_{LIM}$ of 10 cmH$_2$O, the respiratory fluctuations in tracheal pressure increased markedly again when $\dot{V}_{IN}$ was lowered to 15 L/min. at a tracheal pressure limit of 10 cmH$_2$O. The time-based respiratory recordings and corresponding pressure-flow graph are illustrated for the same patient with these settings in FIGS. 27 and 28, respectively. In this example, $P_{LIM}$ exceeds $P_{CRIT}$ minimally. Under these circumstances, the patient is critically dependent on $\dot{V}_{IN}$ meeting his inspiratory flow needs. When a $\dot{V}_{IN}$ of only 15 L/min. is applied during mid-inspiration, the response is suboptimal. This example illustrates a general principle governing the response to specific $\dot{V}_{IN}$ and $P_{LIM}$ levels. As $P_{LIM}$ falls (for a given $\dot{V}_{IN}$), the inspiratory duty cycle of the device will shorten such that greater levels of $\dot{V}_{IN}$ are required to satisfy patient flow demand. A similar shortening of duty cycle will occur as $\dot{V}_{IN}$ rises (for a given $P_{LIM}$).

Thus, we observed that a $\dot{V}_{IN}$ of 15 L/min. and a $P_{LIM}$ of 10 cmH$_2$O will provide adequate inspiratory ventilatory support with a minimum of expiratory washout of CO$_2$ from anatomic dead space. An intermediate level of inspiratory support and CO$_2$ washout can be provided when $\dot{V}_{IN}$ is raised to 45 L/min. at a $P_{LIM}$ of 10 cmH$_2$O, or with a $\dot{V}_{IN}$ of 15 L/min. at a $P_{LIM}$ of 20 cmH$_2$O. Finally, high levels of both inspiratory support and expiratory CO$_2$ washout can be provided by raising both $\dot{V}_{IN}$ to 45 L/min. and $P_{LIM}$ to 20 cmH$_2$O.

From these observations, it is apparent that it should be possible to optimize therapeutic responses by monitoring the tracheal pressure signal. To treat apneic patients initially, higher flow rates are warranted. On the other hand, it is possible to prevent the development of excessively intratracheal high pressure with, for example, a tracheal pressure feedback circuit. This control feature is highly desirable to maximize therapeutic efficacy by reducing the number of glottic apneas, and to maximize safety by preventing pneumothoraces, a complication that arises from excessive lung inflation. In addition, the patient will preferably be given the ability to turn the device on and off as he/she so desires. Moreover, the $\dot{V}_{IN}$ level will preferably be established by physicians with a physiologic titration trial in, for example, a sleep laboratory, and will be prescribed for nocturnal home use thereafter. In addition, the physician will establish the threshold $P_{LIM}$ level above which $\dot{V}_{IN}$ will be automatically stopped or curtailed until $P_{TRACH}$ falls into an acceptable range again.

Figure 29:
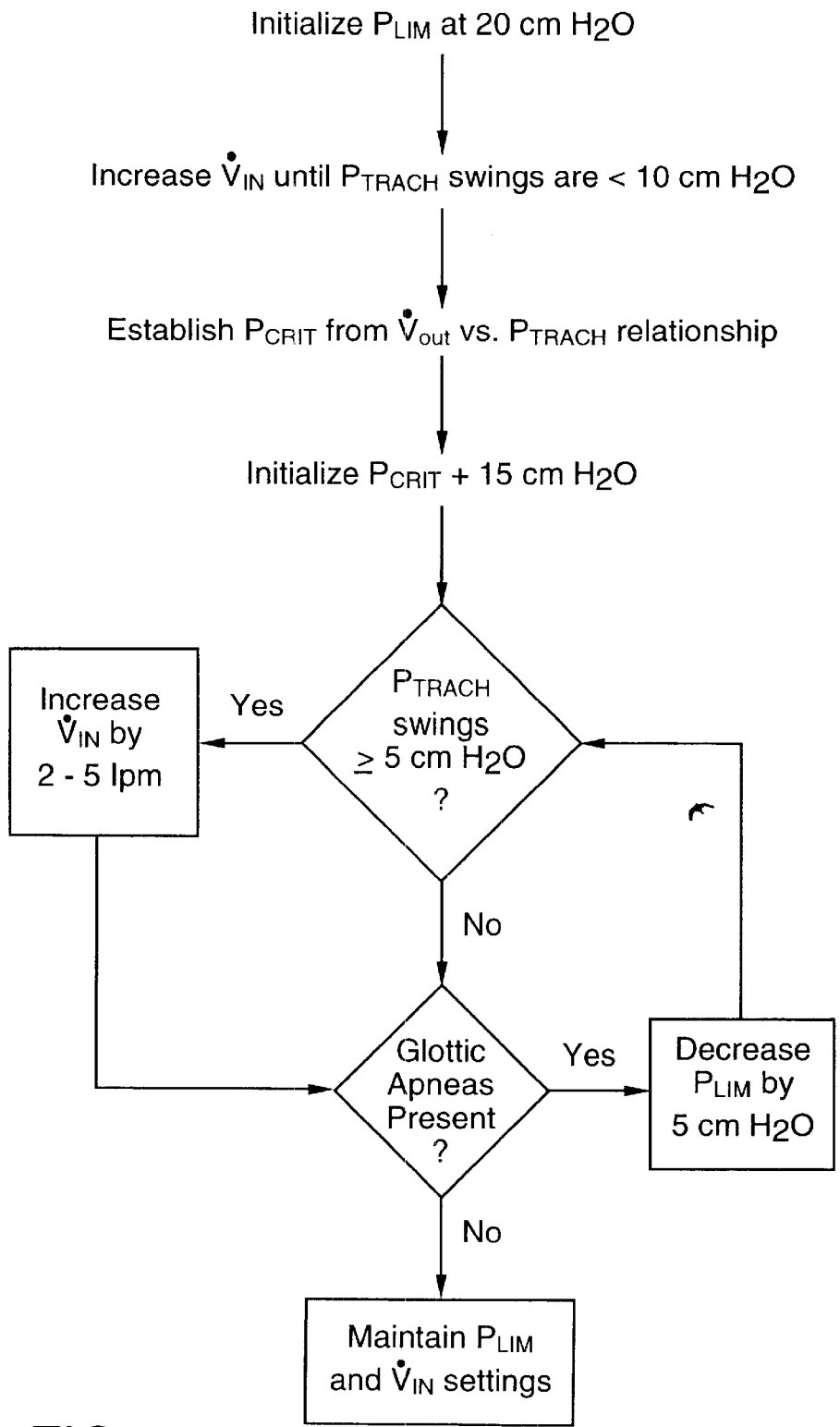
FIG. 29 is a schematic diagram illustrating the establishment of $\dot{V}_{IN}$ and $P_{LIM}$ levels using a titration protocol in accordance with a preferred embodiment of the present invention for patients with obstructive sleep apnea.

A preferred protocol for establishing $\dot{V}_{IN}$ and $P_{LIM}$ during sleep is provided below and summarized in FIG. 29. Standard polysomnography is performed for a patient in whom a transtracheal cannula has been placed. $P_{TRACH}$ and $\dot{V}_{OUT}$ are also monitored continuously during sleep. $P_{LIM}$ is initialized at an initial value of from 0 to about 40 cmH$_2$O, preferably from about 10 to about 30 cmH$_2$O, and more preferably at about 20 cmH$_2$O. $\dot{V}_{IN}$ is titrated upward from zero in steps of about 2 L/min until $P_{TRACH}$ swings are less than from about 5 to 20 cmH$_2$O, preferably less than about 10 cmH$_2$O. $P_{CRIT}$ is established from the $\dot{V}_{OUT}$ versus $P_{TRACH}$ curve of the patient once $P_{CRIT}$ is determined quantitatively. $P_{LIM}$ is then adjusted to a level of from 0 to about 30 cmH$_2$O above $P_{CRIT}$, preferably from about 5 to about 20 cmH$_2$O above $P_{CRIT}$, and more preferably about 15 cmH$_2$O above $P_{CRIT}$.

After initialization of $\dot{V}_{IN}$ and $P_{LIM}$, the tracheal pressure swings are then examined during sleep. If the $P_{TRACH}$ swings remain greater than from about 2 to about 10 cmH$_2$O, preferably greater than about 5 cmH$_2$O, $\dot{V}_{IN}$ is increased in increments of from about 0.5 to about 10 L/min., preferably from about 2 to about 5 L/min. increments. At each step, we monitor for glottic apneas. If they are present, the $P_{LIM}$ is decreased by from about 2 to about 10 cmH$_2$O, preferably about 5 cmH$_2$O. However, we recognized above that a decrease in $P_{LIM}$ may result in greater $P_{TRACH}$ swings. If those $P_{TRACH}$ swings exceed about 5 cmH$_2$O, $\dot{V}_{IN}$ is increased accordingly. The protocol is continued until $P_{TRACH}$ swings are preferably less than about 5 cmH$_2$O and glottic apneas are no longer present. These $\dot{V}_{IN}$ and $P_{LIM}$ settings are then prescribed for nocturnal use by the patient. This protocol is schematically illustrated in FIG. 29.

Once the therapeutic $\dot{V}_{IN}$ and $P_{LIM}$ are established, oxyhemoglobin saturation is preferably monitored. Supplemental oxygen will preferably be titrated to maintain oxyhemoglobin saturation over 90 percent. At the conclusion of the protocol, the following parameters will preferably be prescribed by the physician: (1) $\dot{V}_{IN}$; (2) $P_{LIM}$; and, optionally, (3) $F_1O_2$ (the fraction of inspired oxygen utilized during insufflation).

Figure 30:
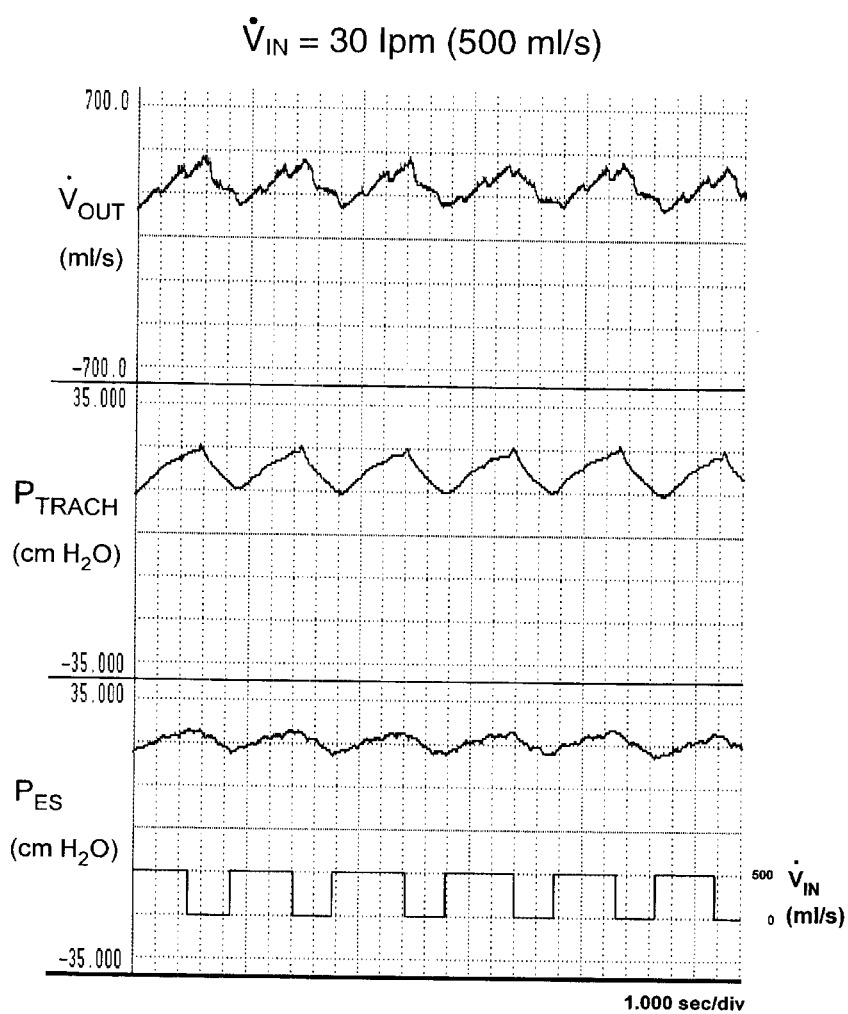
FIG. 30 shows $\dot{V}_{OUT}$, $P_{TRACH}$ and pressure in the esophagus outside the lungs ($P_{ES}$) versus time for a patient with obstructive sleep apnea receiving periodic insufflation in accordance with an embodiment of the present invention during sleep.
Figure 31:
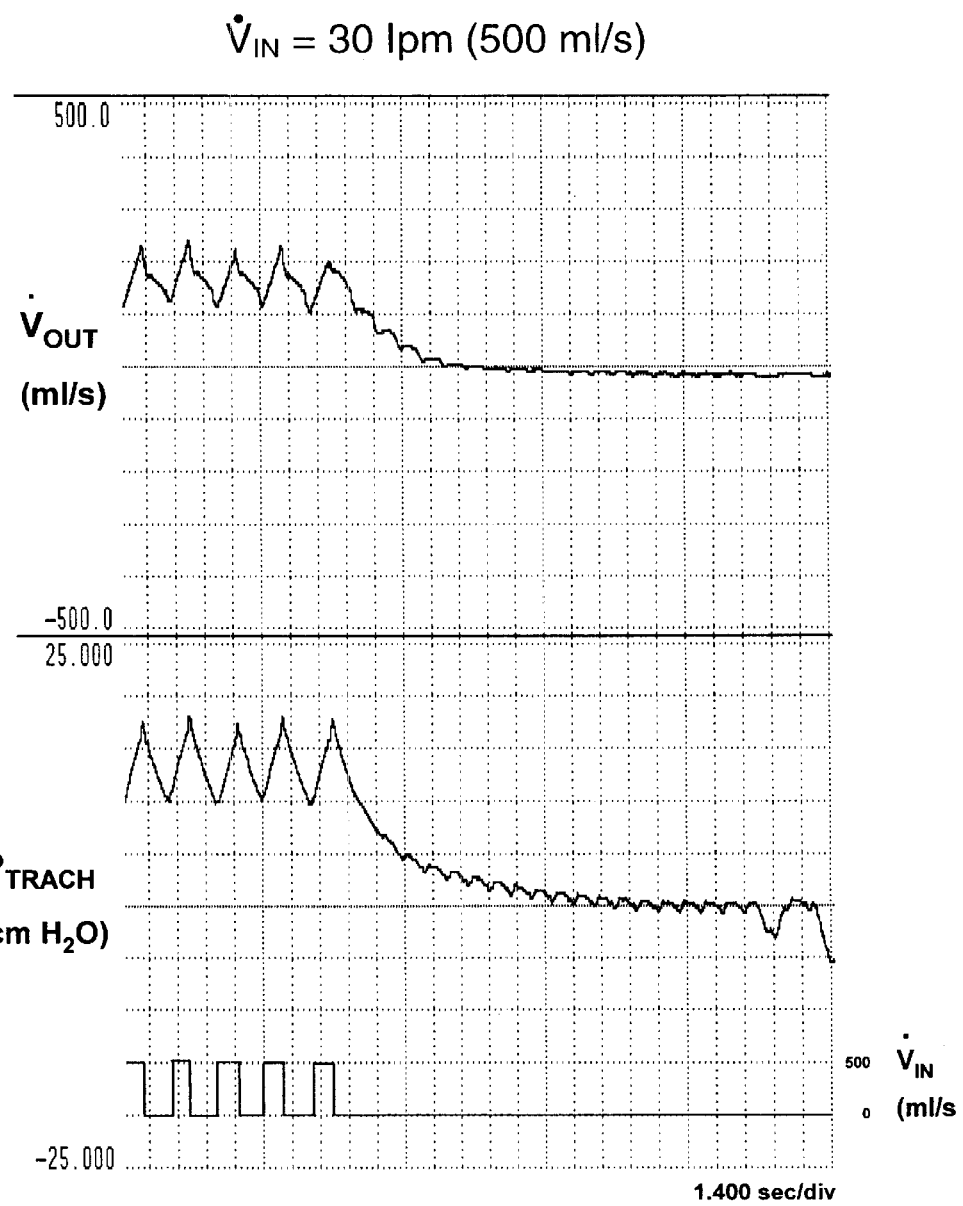
FIG. 31 shows $\dot{V}_{OUT}$, $P_{TRACH}$ and $P_{ES}$, illustrating decay in the same patient represented in FIG. 30 when insufflation flow ($\dot{V}_{IN}$) is abruptly stopped for 5–10 seconds.

We noticed that we could suppress the patient's own inspiratory efforts by abruptly raising $P_{TRACH}$ when insufflation was first applied. We therefore initiated a protocol for generating a passive TTI breathing pattern (PTTI) after setting $\dot{V}_{IN}$ at 30 liters/min, $P_{LIM}$ at 25 cmH$_2$O and the delay period of 2 seconds. With these settings, we observed $P_{TRACH}$ and esophageal pressure ($P_{ES}$) rise and fall in a regular pattern corresponding to the inflation ($\dot{V}_{IN}$ at 30 L/min.) and deflation ($\dot{V}_{IN}$ at 0) phases of the PTTI ventilatory mode (FIG. 30). As $P_{TRACH}$ and PES varied, corresponding increases and decreases in $\dot{V}_{OUT}$ were observed, indicating that air vented through the upper airways in association with changes in $\dot{V}_{IN}$ and $P_{TRACH}$.

To confirm that the patient's spontaneous inspiratory efforts had been suppressed, we abruptly stopped $\dot{V}_{IN}$ for 20 seconds (FIG. 31), as we observed $P_{TRACH}$ and $\dot{V}\dot{V}_{OUT}$ decay. Two key observations were made from the decay of these signals. First, we found that spontaneous inspiratory efforts did not occur for at least 18 seconds, indicating that the patient's own spontaneous respiratory efforts had been suppressed and suggesting that PTTI had provided full ventilatory support. Spontaneous inspiratory dips in $P_{TRACH}$ were observed thereafter (extreme right on recording example FIG. 31). Second, we found that $P_{TRACH}$ decayed exponentially, as described by the relationship:

$$P_{TRACH_t} = P_{TRACH_o} \cdot e^{-kt} + P_{CRIT},$$

where k is $1/\tau$ and $\tau$ is the time constant for emptying of the respiratory system. Our observations in four patients indicate that $\tau$ is closely approximated by the product: $R_s \cdot C_{rs}$. This finding again confirms that the inflation/deflation characteristics of the respiratory system under the PTTI regimen are determined by the passive biomechanical properties of the respiratory system and upper airways. It also indicates that these biomechanical properties can be characterized for the purpose of optimizing the PTTI parameters, $\dot{V}_{IN}$, $P_{LIM}$ and delay time.

For this ventilation mode we consider that the $\dot{V}_{IN}$ level will be set as discussed above. When $\dot{V}_{IN}$ is turned off for exhalation, $P_{TRACH}$ will approach $P_{CRIT}$ asymptotically. For usual values of $K(1/\tau)$ of 0.10 to 0.50 and a $P_{TRACH}$ of 5 to 30 cmH$_2$O, $P_{TRACH}$ after a 1, 2 and 3 second delay period will decay as shown in Table 1.

TABLE 1

| Initial P$_{TRACH}$ | K | FINAL P$_{TRACH}$ (cmH$_2$O) Time Delay Period(s) | | |
|---|---|---|---|---|
| (cmH$_2$O) | (s$^{-1}$) | 1 | 2 | 3 |
| 5 | 0.10 | 4.5 | 4.1 | 3.7 |
| 5 | 0.50 | 3.0 | 1.8 | 1.1 |
| 30 | 0.10 | 27.0 | 24.6 | 22.2 |
| 30 | 0.50 | 18.2 | 11.0 | 6.7 |

Alternatively, the PTTI algorithm also provides the user with the ability to set an expiratory target $P_{TRACH}$ level. Given an initial $P_{TRACH}$ and time constants as shown, the expiratory time required to reach this target $P_{TRACH}$ can be determined from the above data. The foregoing values for K are specific to patients with a positive $P_{CRIT}$. However, as discussed more particularly below, by providing suitable means to selectively block flow out through the trachea, it is expected that results comparable to those in the table above can be achieved.

In accordance with the present invention, we have demonstrated that it is possible to augment ventilation in at least three ways. The first mode of ventilation is effective in patients with complete upper airway obstruction such as obstructive sleep apnea. In this condition, air cannot enter the lungs through the upper airways despite vigorous inspiratory efforts. By providing a substantially constant transtracheal source of airflow, the lungs can inflate during the patient's spontaneous inspiratory efforts. Nevertheless, substantial dips in tracheal pressure have been noted during inspiration when the tracheal source of airflow is inadequate, or glottic apneas have occurred. To overcome this limitation, the $\dot{V}_{IN}$ can be increased, often in conjunction with a lowering of $P_{LIM}$. With the ATTI mode, $\dot{V}_{IN}$ will be applied whenever tracheal pressure is less than $P_{LIM}$ so as to meet the patient's flow demand. We have also recognized periods in which transtracheal insufflation suppresses spontaneous inspiratory efforts completely. When this occurs, we have demonstrated the ability to control ventilation with a third mode, PTTI, which provides a delay time that allows the lungs to deflate spontaneously through the upper airways. After an elapsed time or after $P_{TRACH}$ declines sufficiently, insufflation flow is reapplied and tracheal pressure rises accordingly. Thus, various modes are provided which support and augment ventilation by permitting lung inflation from the transtracheal air course and lung deflation through the upper airways.

Figure 32:
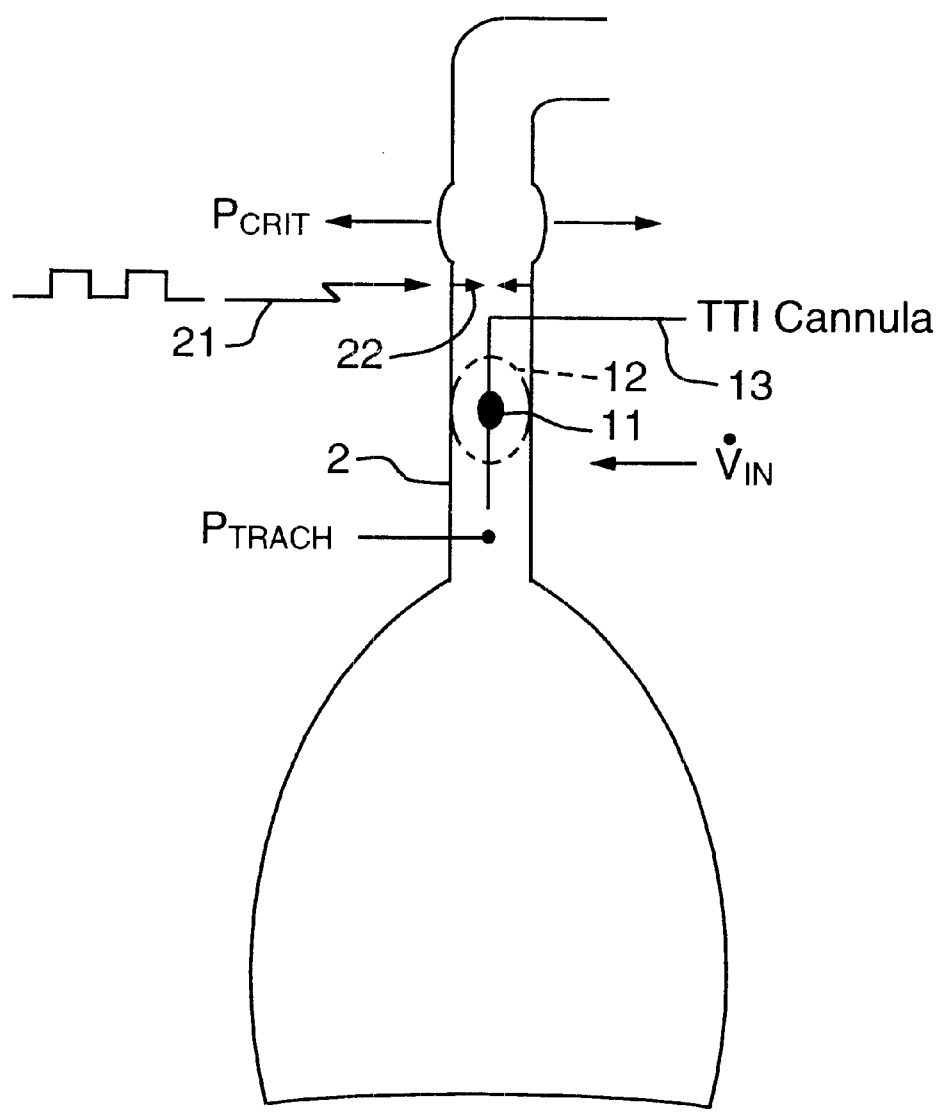
FIG. 32 is a schematic diagram showing devices for selectively blocking the trachea of a patient in accordance with embodiments of the present invention.

As explained hereinabove, the reported data was collected from patients with obstructive sleep apnea that had a rather unique upper airway physiology that is characterized by the development of a positive $P_{CRIT}$ (the airway is closed) during sleep. When the upper airway is closed, transtracheal insufflation in accordance with the invention will expand the lungs. In patients in whom $P_{CRIT}$ is negative, air will freely discharge through the upper airways when $\dot{V}_{IN}$ is applied. Under these circumstances, TTI will hardly help inflate the lungs as patients breath spontaneously. Inflation can be facilitated, however, in one of at least two ways. First, tracheal airflow resistance may be increased. As shown in FIG. 32, this can be accomplished by providing an inflatable balloon 11 or cuff in the trachea 2 connected to a catheter 13 (such as a balloon on the end of a Swan Ganz catheter) and selectively inflating the same, as shown in phantom 12, to partially or completely block the flow of air out through the upper airways. The size of the balloon would be adjusted so as to increased tracheal resistance sufficiently to inflate the lungs. During exhalation, the balloon can be deflated, reducing tracheal airflow resistance and allowing for greater discharge of air through the upper airways. Alternatively, a constant partial outflow obstruction to TTI flow can be provided by maintaining the balloon partially inflated throughout the respiratory cycle. Thus, intermittent inflation and deflation or continuous inflation with partial obstruction of the trachea can be performed to augment ventilation or to statically elevate lung volume and washout $CO_2$ during transtracheal insufflation in patients with a negative $P_{CRIT}$, respectively.

In the alternative embodiment shown in FIG. 32, suitable electrodes 21 may be used to selectively stimulate the laryngeal adductor muscles electrically, to selectively close the glottis 22. Glottic closure in turn prevents the leakage of airflow through the upper airways. $\dot{V}_{IN}$ can then be directed to the lungs, leading to progressive lung inflation. After a set tidal volume is delivered or tracheal pressure is reached, stimulation of the adductors can be discontinued, thus allowing the vocal cords to open and the lungs to deflate. Thus, intermittent electrical stimulation of the laryngeal adductor muscles can augment ventilation during transtracheal insufflation in patients with a negative $P_{CRIT}$.

Regardless of the method of decreasing leakage out the upper airways, inflation and deflation of the lungs will proceed without any work expenditure by the respiratory pump muscles, e.g., the diaphragm. This means that the work of breathing during transtracheal insufflation remains zero, as the patient's respiratory muscles need not contract to either inflate or deflate the lungs. It is therefore possible to completely unload the respiratory muscles and support/augment ventilation with transtracheal insufflation.

While the invention has been described in connection with what is presently considered to be the most practical and preferred embodiments, it is to be understood that the invention is not to be limited to the disclosed embodiments, but on the contrary is intended to cover various modifications and equivalent arrangements included within the spirit and scope of the appended claims. Indeed, the invention may be advantageously utilized in supporting ventilation of patients with breathing disorders other than obstructive sleep apnea, such as patients with obstructive or restrictive lung disease, chest wall, neuromuscular, and neurologic diseases, and other sleep related breathing disorders. Furthermore, the present system may be used to treat patients under anesthesia, patients requiring full ventilatory support, patients requiring cardiopulmonary resuscitation, patients requiring speech or voice augmentation, patients requiring facilitation of mucociliary clearance, and the like.

What is claimed is:

1. A method of providing interactive ventilatory support to a patient based on the physiological requirements of the patient, the method comprising:

initially determining a degree of obstruction in an upper airway of the patient; and subsequently delivering a controlled rate of flow of breathing gas directly to the trachea of the patient below the location of potential obstruction based on the gas pressure measured directly in the trachea of the patient and the determined degree of obstruction in the upper airway of the patient in order to facilitate exhalation through the upper airway of the patient.

2. The method of claim 1, further comprising delivering the controlled flow of breathing gas transtracheally to the patient.

3. The method of claim 1, further comprising:

establishing a tracheal gas pressure limit for the patient;

establishing a breathing gas flow rate value for the patient;

delivering the breathing gas to the patient at the breathing gas flow rate value when the gas pressure in the trachea of the patient is below the tracheal gas pressure limit; and reducing the flow of breathing gas to the patient when the gas pressure in the trachea of the patient reaches the tracheal gas pressure limit.

4. The method of claim 3, further comprising:

establishing a critical tracheal gas pressure level of the patient; and establishing the tracheal gas pressure limit above the critical tracheal gas pressure level.

5. The method of claim 3, further comprising resuming the flow of breathing gas after a delay period subsequent to the reduction of the flow of breathing gas.

6. The method of claim 3, further comprising establishing an expiratory target tracheal gas pressure level below the tracheal gas pressure limit; and resuming the flow of breathing gas when the gas pressure in the trachea of the patient reaches the expiratory target tracheal gas pressure.

7. The method of claim 1, further comprising substantially continuously monitoring the gas pressure in the trachea.

8. The method of claim 1, wherein the determination of whether the upper airway of the patient is obstructed comprises measuring gas pressure in the trachea of the patient while providing gas to the trachea at a controlled flow rate.

9. The method of claim 1, wherein the controlled rate of breathing gas is delivered to the patient below a potential obstruction in the upper airway of the patient.

10. A method of providing breathing gas to a patient comprising:

inserting a catheter into the trachea of a patient;

initially determining a critical tracheal gas pressure level of the patient below which the upper airway of the patient occludes;

initially establishing a tracheal gas pressure limit for the patient;

measuring gas pressure directly in the trachea; and subsequently controlling rate of flow of the breathing gas delivered directly to the trachea below a potential obstruction in the upper airway of the patient through the catheter based on the critical tracheal gas pressure level of the patient and the measured gas pressure in the trachea in order to provide an adequate supply of breathing gas to the patient and to facilitate exhalation through the upper airway of the patient.

11. The method of claim 10, further comprising inserting the catheter transtracheally into the trachea of the patient.

12. The method of claim 10, further comprising establishing a breathing gas flow rate value for the patient.

13. The method of claim 12, further comprising:

substantially continuously monitoring the gas pressure in the trachea.

14. The method of claim 12, further comprising:

storing information corresponding to the measured gas pressure in the trachea.

15. The method of claim 12, wherein the breathing gas comprises from about 21 to 100 percent oxygen.

16. The method of claim 12, further comprising humidifying the breathing gas.

17. The method of claim 12, further comprising heating the breathing gas to approximately the same temperature as the body temperature of the patient.

18. The method of claim 12, further comprising employing the method on a patient suffering from obstructive sleep apnea.

19. The method of claim 12, further comprising establishing the tracheal gal pressure limit and the breathing gas flow rate value by:

initializing the tracheal gas pressure limit at an initial value;

increasing the breathing gas flow rate until swings in the measured gas pressure in the trachea are less than a predetermined value;

adjusting the initial tracheal gas pressure limit to a predetermined pressure value above the critical tracheal gas pressure level of the patient;

increasing the breathing gas flow rate if swings in the measured gas pressure in the trachea are greater than a predetermined value;

maintaining the tracheal gas pressure limit and breathing gas flow rate value if the patient experiences substantially no glottic apneas; and decreasing the tracheal gas pressure limit by a predetermined amount if the patient experiences substantial glottic apneas.

20. The method of claim 19, further comprising:

initializing the tracheal gas pressure limit at an initial value of from about 10 to about 30 cmH$_2$O;

increasing the breathing gas flow rate until the swings in the measured gas pressure in the trachea are less than a predetermined value of from about 5 to about 20 cmH$_2$O;

adjusting the initial tracheal gas pressure limit to a predetermined pressure value of from 0 to about 20 cmH$_2$O above the critical tracheal gas pressure level of the patient;

increasing the breathing gas flow rate from about 0.5 to about 10 liters/minute if the swings in the measured gas pressure in the trachea are greater than a predetermined value of from about 2 to about 10 cmH$_2$O; and decreasing the tracheal gas pressure limit by a predetermined amount of from about 2 to about 10 cmH$_2$O if the patient experiences substantial glottic apneas.

21. The method of claim 12, wherein the breathing gas flow rate value is substantially constant.

22. The method of claim 12, wherein the breathing gas flow rate value is from about 4 to about 60 liters per minute.

23. The method of claim 12, further comprising reducing the flow of breathing gas when the measured gas pressure in the trachea reaches the tracheal gas pressure limit.

24. The method of claim 12, further comprising terminating the flow of breathing gas when the measured gas pressure in the trachea reaches the tracheal gas pressure limit.

25. The method of claim 12, further comprising:

establishing a maximum tracheal gas pressure value for the patient; and terminating the flow of breathing gas when the measured gas pressure in the trachea reaches the maximum tracheal gas pressure value.

26. The method of claim 12, further comprising:

establishing the tracheal gas pressure limit above the critical tracheal gas pressure level.

27. The method of claim 26, wherein the critical tracheal gas pressure level is not less than 5 cmH$_2$O below atmospheric pressure.

28. The method of claim 26, wherein this critical tracheal gas pressure level is below atmospheric pressure.

29. The method of claim 28, further comprising at least partially blocking flow of gas through the upper airway of the patient.

30. The method of claim 26, wherein the tracheal gas pressure limit is from 0 to abut 30 cmH$_2$O above the critical tracheal gas pressure level.

31. The method of claim 26, wherein the tracheal gas pressure limit is from about 5 to about 20 cmH$_2$O above the critical tracheal gas pressure level.

32. The method of claim 10, wherein the critical tracheal gas pressure level is above atmospheric pressure.

33. The method of claim 12, further comprising:

reducing the flow of breathing gas when the measured gas pressure in the trachea reaches the tracheal gas pressure limit; and subsequently increasing the flow of breathing gas after a delay period.

34. The method of claim 33, wherein the delay period is from about 0.5 to 10 seconds.

35. The method of claim 33, further comprising:

terminating the flow of breathing gas when the measured gas pressure in the trachea reaches the tracheal gas pressure limit; and resuming the flow of breathing gas at a substantially constant flow rate after the delay period.

36. The method of claim 12, further comprising:

establishing an expiratory target tracheal gas pressure level below the tracheal gas pressure limit;

reducing the flow of breathing gas when the measured gas pressure in the trachea reaches the tracheal gas pressure limit; and subsequently increasing the flow of breathing gas when the measured gas pressure in the trachea reaches the expiratory target tracheal gas pressure level.

37. The method of claim 36, wherein the expiratory target tracheal gas pressure is from about 2 to about 40 cmH$_2$O below the tracheal gas pressure limit.

38. The method of claim 36, further comprising:

terminating the flow of breathing gas when the measured gas pressure in the trachea reaches the tracheal gas pressure limit; and resuming the flow of breathing gas at a substantially constant flow rate when the measured gas pressure in the trachea reaches the expiratory target tracheal gas pressure level.

39. The method of claim 36, further comprising:

establishing a critical tracheal gas pressure level of the patient; and establishing the differential tracheal gas pressure level above the critical tracheal gas pressure level.

40. Apparatus for providing breathing gas to a patient comprising:

means for determining a critical tracheal gas pressure level of the patient below which the upper airway of the patient occludes;

means for delivering breathing gas directly into the trachea of the patient below a potential obstruction in the upper airway of the patient;

means for measuring gas pressure directly in the trachea; and means for subsequently controlling rate of flow of the breathing gas through the breathing gas delivery means directly into the trachea based on the critical tracheal gas pressure level of the patient and the measured gas pressure in the trachea in order to provide an adequate supply of breathing gas to the patient and to facilitate exhalation through the upper airway of the patient.

41. The apparatus of claim 40, wherein the breathing gas delivery means comprises a transtracheal catheter.

42. The apparatus of claim 41, wherein transtracheal catheter comprises a proximal end connected to a source of the breathing gas and a distal end for insertion through the trachea of the patient, and the gas pressure measuring means comprises a pressure sensor mounted on the distal end of the catheter.

43. The apparatus of claim 40, wherein the flow controlling means comprises means for intermittently delivering the breathing gas through the breathing gas delivery means into the trachea at a prescribed gas flow rate value.

44. The apparatus of claim 43, wherein the gas flow rate value is substantially constant.

45. The apparatus of claim 40, wherein the flow controlling means comprises means for reducing the flow of the breathing gas when the measured gas pressure reaches a prescribed tracheal gas pressure limit.

46. The apparatus of claim 45, wherein the flow controlling means comprises means for subsequently increasing the flow of the breathing gas after a prescribed delay period.

47. The apparatus of claim 45, wherein the flow controlling means comprises means for subsequently increasing the flow of the breathing gas after the measured gas pressure falls to a prescribed expiratory target tracheal pressure level below the tracheal gas pressure limit.

48. The apparatus of claim 40, further comprising means for at least partially blocking flow of gas through the upper airway of the patient.

49. The apparatus of claim 40, further comprising means for substantially continuously monitoring the gas pressure in the trachea.

50. The apparatus of claim 40, further comprising means for storing information corresponding to the measured gas pressure in the trachea.

51. The apparatus of claim 40, further comprising means for humidifying the breathing gas prior to delivery of the breathing gas into the trachea.

52. The apparatus of claim 40, further comprising means for heating the breathing gas to approximately the same temperature as the body temperature of the patient prior to delivery of the breathing gas into the trachea.

53. Apparatus for providing breathing gas to a patient comprising:

a source of breathing gas;

a catheter in flow communication with the source of the breathing gas having a distal end structured and configured for placement below a potential obstruction in the upper airway of the patient;

an upper airway flow sensor structured and configured for placement above the potential obstruction for measuring an initial gas flow rate through the upper airway of the patient;

a tracheal pressure sensor structured and configured for placement in the trachea of the patient for measuring gas pressure directly in the trachea of the patient; and a breathing gas flow controller operatively coupled to the source of breathing gas and the tracheal pressure sensor for controlling the rate of flow of the breathing gas delivered directly to the trachea below the potential obstruction from the source of breathing gas through the catheter based on the initial gas flow rate through the upper airway and the measured gas pressure in the trachea in order to provide an adequate supply of breathing gas to the patient and to facilitate exhalation through the upper airway of the patient.

54. The apparatus of claim 53, further comprising a valve in flow communication with the source of breathing gas and the catheter, and operatively coupled to the flow controller for reducing and increasing the flow of the breathing gas through the catheter.

55. The apparatus of claim 53, wherein the catheter is a transtracheal catheter.

56. The apparatus of claim 53, further comprising a monitor operatively coupled to the tracheal pressure sensor for substantially continuously monitoring the gas pressure in the trachea.

* * * * *

UNITED STATES PATENT AND TRADEMARK OFFICE
Certificate

Patent No. 6,457,472 B1                                         Patented: October 1, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Alan R. Schwartz, Baltimore, MD; Philip L. Smith, Baltimore, MD; and Hartmut Schneider, Lutherville, MD.

Signed and Sealed this Twenty-third Day of August 2005.

*TATYANA ZALUKAEVA*
*Supervisory Patent Examiner*
Art Unit 3761

UNITED STATES PATENT AND TRADEMARK OFFICE
CERTIFICATE OF CORRECTION

PATENT NO. : 6,457,472 B1
DATED : October 1, 2002
INVENTOR(S) : Alan R. Schwartz and Philip L. Smith It is certified that error appears in the above-identified patent and that said Letters Patent is hereby corrected as shown below:

Title page,
Item [56], References Cited, U.S. PATENT DOCUMENTS,
"4,456,008" reference, "Clowson et al." should read -- Clawson et al. --;
"5,297,288" reference, "5,297,288    3/1994" should read
-- 5,279,288    1/1994 --; and
"5,515,844" reference, "Chirstopher" should read -- Christopher --.
OTHER PUBLICATIONS,
"Heimlich et al.," reference, "Plumonary" should read -- Pulmonary --;
"Bloom et al.," reference, "Plumonary" should read -- Pulmonary --;
"American Thoracic Society," reference, "Car" should read -- Care --; and
"Gay et al.," reference, "Pulomonary" should read -- Pulmonary --.

Column 8,
Line 66, "th e" should read -- the --.

Column 11,
Line 2, "$P_{LIM}$is" should read -- $P_{LIM}$ is --.

Column 12,
Line 11, "$\dot{V}$" should read -- $\dot{V}_{IN}$ --

Line 16, "$V_{IN}$is" should read -- $V_{IN}$ is --.

Column 18,
Line 40, "$CO_2O$" should read -- $CO_2$ --.

Column 19,

Line 17, " $\dot{V}_{OUT}$ of" should read -- $\dot{V}_{OUT}$ of --.

Line 28, "$P_{TRACH}$falls" should read -- $P_{TRACH}$ falls --.

Column 20,
Line 7, "$P_{LIM}$of" should read -- $P_{LIM}$ of" --.

Column 21,
Line 16, "PES" should read -- $P_{ES}$ --.

Line 22, "$V \dot{V}_{OUT}$" should read -- $\dot{V}_{OUT}$ --.

UNITED STATES PATENT AND TRADEMARK OFFICE
CERTIFICATE OF CORRECTION

PATENT NO. : 6,457,472 B1
DATED : October 1, 2002
INVENTOR(S) : Alan R. Schwartz and Philip L. Smith It is certified that error appears in the above-identified patent and that said Letters Patent is hereby corrected as shown below:

Column 22,

Line 19, " $\dot{V}_{IN}$ can" should read -- $\dot{V}_{IN}$ can --.

Column 24,
Line 54, "gal" should read -- gas --.

Column 25,
Line 44, "establishing the tracheal gas pressure limit above the critical tracheal gas pressure level" should read -- maintaining the pressure in the treachea of the patient at a level between the critical tracheal gas pressure level and the tracheal gas pressure limit --.

Column 26,
Line 2, "The method of claim 33, wherein the delay period is from about 0.5 to 10 seconds." should read -- The method of claim 33, wherein the delay period is from about 0.5 to about 10 seconds. --.

Signed and Sealed this

Thirty-first Day of January, 2006

JON W. DUDAS
*Director of the United States Patent and Trademark Office*